United States Patent
Sjölin

(10) Patent No.: US 11,255,981 B2
(45) Date of Patent: Feb. 22, 2022

(54) TOTAL TIME-OVER-THRESHOLD (TTOT) PROCESSING FOR A PHOTON-COUNTING X-RAY DETECTOR

(71) Applicant: Prismatic Sensors AB, Stockholm (SE)

(72) Inventor: Martin Sjölin, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 17/092,752

(22) Filed: Nov. 9, 2020

(65) Prior Publication Data

US 2021/0239856 A1    Aug. 5, 2021

Related U.S. Application Data

(60) Provisional application No. 62/970,308, filed on Feb. 5, 2020.

(51) Int. Cl.
*G01T 1/17*    (2006.01)
*G01T 1/24*    (2006.01)
*A61B 6/00*    (2006.01)

(52) U.S. Cl.
CPC .............. *G01T 1/17* (2013.01); *G01T 1/247* (2013.01); *A61B 6/4241* (2013.01); *A61B 6/482* (2013.01)

(58) Field of Classification Search
CPC .......... G01T 1/17; G01T 1/247; A61B 6/482; A61B 6/4241
See application file for complete search history.

(56) References Cited

U.S. PATENT DOCUMENTS

| | | | |
|---|---|---|---|
| 9,535,167 B2 | 1/2017 | Proksa et al. | |
| 9,678,220 B2 | 6/2017 | Herrmann | |
| 2009/0304149 A1 | 12/2009 | Herrmann et al. | |
| 2011/0036988 A1 | 2/2011 | Campbell et al. | |
| 2012/0085915 A1 | 4/2012 | Baeumer et al. | |
| 2014/0328465 A1 | 11/2014 | Herrmann | |
| 2015/0063527 A1* | 3/2015 | Daerr | G01T 1/248 378/5 |
| 2015/0063533 A1* | 3/2015 | Proksa | G01T 1/1606 378/19 |
| 2019/0154852 A1* | 5/2019 | McCroskey | G01T 1/2985 |

FOREIGN PATENT DOCUMENTS

EP    1 231 485    8/2002

OTHER PUBLICATIONS

Bergamaschi et al., Time-over-threshold readout to enhance the high flux capabilities of single-photon-counting detectors, 2011, J. Synchrotron Rad., vol. 18, pp. 923-929 (Year: 2011).*

(Continued)

*Primary Examiner* — Christine S. Kim
(74) *Attorney, Agent, or Firm* — Nixon & Vanderhye

(57) ABSTRACT

There is provided a circuit (502; 503; 504) configured for operation with a multi-bin photon-counting x-ray detector (20) having multiple energy thresholds, wherein said circuit (502; 503; 504) is configured to obtain or generate several Total Time-Over-Threshold (TTOT) signals corresponding to several different energy thresholds, and provide energy integrating information based on said several TTOT signals.

8 Claims, 16 Drawing Sheets

(56) References Cited

OTHER PUBLICATIONS

Gaudin et al., Dual-Threshold Time-over-Threshold Nonlinearity Correction for PET Detectors, Aug. 11, 2020, Nucl Instrum Methods Phys Res A., pp. 1-16 (Year: 2020).*

Hsieh et al., "Spectral resolution and high-flux capability tradeoffs in CdTe detectors for clinical CT," Medical physics, vol. 45, No. 4, pp. 1433-1443, 2018.

Kraft et al., "Counting and integrating readout for direct conversion x-ray imaging: Concept, realization and first prototype measurements," IEEE Transactions on Nuclear Science, vol. 54, No. 2, pp. 383-390, 2007.

Krüger et al., "Cix: a detector for spectrally enhanced x-ray imaging by simultaneous counting and integrating," in Medical Imaging 2008: Physics of Medical Imaging, vol. 6913. International Society for Optics and Photonics, 2008, 13 pages.

Fint et al., "Comparison of Pixelated CdZnTe, CdTe and Si Sensors With the Simultaneously Counting and Integrating CIX Chip," IEEE Transactions on Nuclear Science, vol. 56, No. 6, pp. 3819-3827, 2009.

Roessl et al., "A comparative study of a dual-energy-like imaging technique based on counting-integrating readout," Medical physics, vol. 38, No. 12, pp. 6416-6428, 2011.

Wong et al., "Electrical measurements of a multi-mode hybrid pixel detector ASIC for radiation detection," Journal of Instrumentation, vol. 7, No. 01, Jan. 13, 2012, 9 pages.

Bergamaschi et al., "Beyond single photon counting x-ray detectors," Nuclear Instruments and Methods in Physics Research Section A: Accelerators, Spectrometers, Detectors and Associated Equipment, vol. 628, pp. 238-241, 2011.

Kappler et al., "First results from a hybrid prototype ct scanner for exploring benefits of quantum-counting in clinical CT," in Medical Imaging 2012: Physics of Medical Imaging, vol. 8313. International Society for Optics and Photonics, 2012, 12 pages.

Chu et al., "Combination of current integrating/ photon-counting detector modules for spectral CT," Physics in Medicine & Biology, vol. 58, No. 19, 2013, pp. 7009-7024.

Li et al., "Spectral CT modeling and reconstruction with hybrid detectors in dynamic-threshold-based counting and integrating modes," IEEE transactions on medical imaging, vol. 34, No. 3, pp. 716-728, 2015.

Akesson et al., "Particle identification using the time-over-threshold method in the ATLAS transition radiation tracker," Nuclear Instruments and Methods in Physics Research Section A: Accelerators, Spectrometers, Detectors and Associated Equipment, vol. 474, No. 2, pp. 172-187, 2001.

Liopart et al., "Timepix, a 65k programmable pixel readout chip for arrival time, energy and/or photon counting measurements," Nuclear Instruments and Methods in Physics Research Section A: Accelerators, Spectrometers, Detectors and Associated Equipment, vol. 581, pp. 485-494, 2007.

Jakubek, "Precise energy calibration of pixel detector working in time-over-threshold mode," Nuclear Instruments and Methods in Physics Research Section A: Accelerators, Spectrometers, Detectors and Associated Equipment, vol. 633, pp. S262-S266, 2011.

Wong et al., "A pixel detector asic for dosimetry using time-over-threshold energy measurements," Radiation Measurements, vol. 46, No. 12, pp. 1619-1623, 2011.

Shimazoe et al., "Dynamic time over threshold method," IEEE Transactions on Nuclear Science, vol. 59, No. 6, pp. 3213-3217, 2012.

Yonggang et al., "A Linear Time-Over-Threshold Digitizing Scheme and Its 64-channel DAQ Prototype Design on FPGA for a Continuous Crystal PET Detector," IEEE transactions on nuclear science, vol. 61, No. 1, pp. 99-106, 2014.

Bourlis et al., "Use of multi-time over threshold electronics to digitize signals from a very large volume undersea neutrino telescope," Nuclear Instruments and Methods in Physics Research Section A: Accelerators, Spectrometers, Detectors and Associated Equipment, vol. 626-627, pp. S163-S165, 2011.

Ferry et al., "Multi-timeover-threshold technique for photomultiplier signal processing: Description and characterization of the SCOTT ASIC," Nuclear Instruments and Methods in Physics Research Section A: Accelerators, Spectrometers, Detectors and Associated Equipment, vol. 695, pp. 52-60, 2012.

Kim et al., "Analog and digital signal processing method using multi-time-over threshold and FPGA for PET," Medical physics, vol. 45, No. 9, pp. 4104-4111, 2018.

Georgakopoulou et al., "A 100-ps multi-time over threshold data acquisition system for cosmic ray detection," Measurement Science and Technology, vol. 29, No. 11, 2018, 23 pages.

Bergamaschi et al., "Time over-threshold readout to enhance the high flux capabilities of single photon-counting detectors," Journal of synchrotron radiation, vol. 18, No. 6, pp. 923-929, 2011.

Hsieh et al., "Improving pulse detection in multibin photon-counting detectors", Journal of Medical Imaging, vol. 3, No. 2, 2016, 8 pages.

Tenney, "Idealized pulse pileup effects on energy spectra", Nuclear Instruments and Methods in Physics Research, vol. 219, pp. 165-172, 1984.

International Search Report for PCT/SE2020/051080 dated Dec. 29, 2020, 5 pages.

Written Opinion of the ISA for PCT/SE2020/051080 dated Dec. 29, 2020, 5 pages.

Turecek et al., "Dependence on temperature and pixel threshold of the calibration for the Timepix detector and its correction method," Journal of Instrumentation, Jan. 7, 2013, 8 pages.

Zuber et al., "Characterization of a 2x3 Timepix assembly with a 500μm thick silicon sensor," Journal of Instrumentation, May 20, 2014, 9 pages.

* cited by examiner

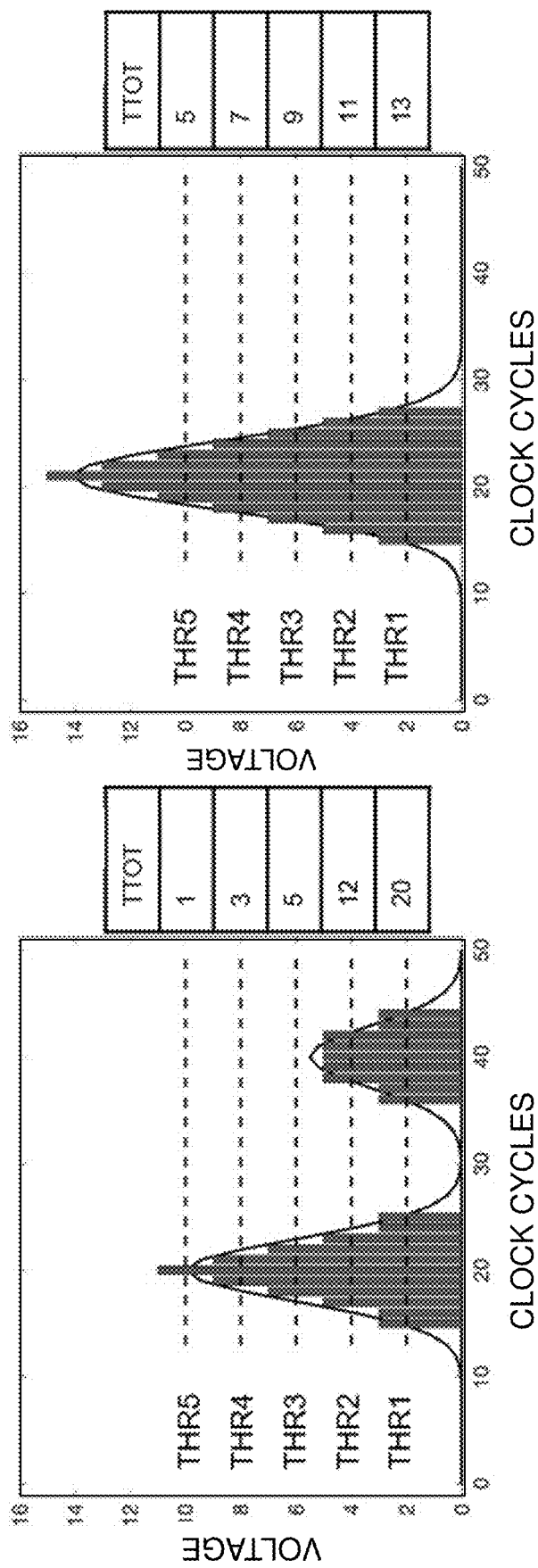

TOTAL TIME-OVER-THRESHOLD (TTOT) PROCESSING FOR A PHOTON-COUNTING X-RAY DETECTOR

CROSS-REFERENCE TO RELATED PATENT APPLICATION

This application claims the benefit of priority under 35 USC § 119(e) of U.S. provisional patent application No. 62/970,308 filed Feb. 5, 2020, the entire contents of which is hereby incorporated by reference.

TECHNICAL FIELD

The proposed technology relates to a measurement method to be performed, e.g. in an x-ray imaging system. The proposed technology also relates to corresponding circuits, devices and/or systems as well as a related computer program and computer program product.

BACKGROUND

Radiographic imaging such as x-ray imaging has been used for years in medical applications and for non-destructive testing.

Normally, an x-ray imaging system includes an x-ray source and an x-ray detector array consisting of multiple detectors comprising one or many detector elements (independent means of measuring x-ray intensity/fluence). The x-ray source emits x-rays, which pass through a subject or object to be imaged and are then registered by the detector array. Since some materials absorb a larger fraction of the x-rays than others, an image is formed of the subject or object.

A challenge for x-ray imaging detectors is to extract maximum information from the detected x-rays to provide input to an image of an object or subject where the object or subject is depicted in terms of density, composition and structure.

In a typical medical x-ray imaging system, the x-rays are produced by an x-ray tube. The energy spectrum of a typical medical x-ray tube is broad and ranges from zero up to 160 keV. The detector therefore typically detects x-rays with varying energy. It may be useful with a brief overview of an illustrative overall x-ray imaging system with reference to FIG. 1. In this illustrative, but non-limiting, example the x-ray imaging system 100 basically comprises an x-ray source 10, an x-ray detector system 20 and an associated image processing system or device 30. In general, the x-ray detector system 20 is configured to register radiation from the x-ray source 10, which optionally has been focused by optional x-ray optics and passed an object, a subject or a part thereof. The x-ray detector system 20 is connectable to the image processing system 30 via suitable analog and read-out electronics, which is at least partly integrated in the x-ray detector system 20, to enable image processing and/or image reconstruction by the image processing system 30.

There is a general demand for improved performance of x-ray detectors and/or x-ray imaging systems. In particular, it is desirable to be able to make optimal use of the photon interaction information from the x-ray detector.

SUMMARY

It is a general object to improve the performance of x-ray detectors and/or x-ray imaging systems.

For example, it is desirable to provide new, useful signal information from a multi-bin photon-counting x-ray detector.

It may also be desirable to be able to improve the performance of a multi-bin photon counting detector, especially at high photon rates.

It is a specific object to provide a general circuit configured for operation with a multi-bin photon-counting x-ray detector.

Another object is to provide a Total Time-Over-Threshold (TTOT) logic circuit configured for operation with a multi-bin photon-counting x-ray detector.

Yet another object is to provide a digital processing circuit configured for operation with a multi-bin photon-counting x-ray detector.

Still another object is to provide a measurement circuit for a photon-counting x-ray detector.

It is also an object to provide an overall x-ray imaging system comprising such circuitry.

Another object is to provide a system configured for operation with a multi-bin photon-counting x-ray detector.

A further object is to provide a method of obtaining energy integrating information from a multi-bin photon-counting x-ray detector.

It is also an object to provide a corresponding computer program and/or computer-program product.

These and other objects may be achieved by one or more embodiments of the proposed technology.

According to a first aspect, there is provided a circuit configured for operation with a multi-bin photon-counting x-ray detector having multiple energy thresholds. The circuit is configured to obtain or generate several Total Time-Over-Threshold (TTOT) signals corresponding to several different energy thresholds, and provide energy integrating information based on said several TTOT signals.

According to a second aspect, there is provided a Total Time-Over-Threshold (TTOT) logic circuit configured for operation with a multi-bin photon-counting x-ray detector having multiple energy thresholds, wherein said TTOT logic circuit is configured to generate several Total Time-Over-Threshold (TTOT) signals corresponding to several different energy thresholds, and provide energy integrating information based on said several TTOT signals.

According to a third aspect, there is provided a digital processing circuit configured for operation with a multi-bin photon-counting x-ray detector having multiple energy thresholds, wherein the digital processing circuit is configured to obtain more than one Total Time-Over-Threshold (TTOT) signal corresponding to more than one energy threshold, and provide energy integrating information based on said more than one TTOT signal.

According to a fourth aspect, there is provided a measurement circuit for a photon-counting x-ray detector comprising a TTOT logic circuit of the second aspect and/or a digital processing circuit of the third aspect.

According to a fifth aspect, there is provided an x-ray imaging system comprising a circuit of any of the first aspect, second aspect, third aspect and/or fourth aspect.

According to a sixth aspect, there is provided a system configured for operation with a multi-bin photon-counting x-ray detector having multiple energy thresholds, wherein the system is configured for generating more than one Total Time-Over-Threshold (TTOT) signal based on the output from more than one comparator of the multi-bin photon-counting detector.

According to a seventh aspect, there is provided a method of obtaining energy integrating information from a multi-bin photon-counting x-ray detector, wherein the method comprises providing or generating a signal that represents or approximates an energy integrating signal based on Total Time-Over-Threshold (TTOT) signals for several energy thresholds set at different energies in the multi-bin photon-counting detector.

According to an eighth aspect, there is provided a computer program comprising instructions, which when executed by a processor, cause the processor to perform the method of the seventh aspect.

According to a ninth aspect, there is provided a computer-program product comprising a non-transitory computer-readable medium having stored thereon a computer program of the eighth aspect.

In this way, it is possible to obtain a signal that represents or approximates an energy integrating signal based on Total Time-Over-Threshold (TTOT) signals for several energy thresholds set at different energies in a multi-bin photon-counting x-ray detector. Such a signal may be referred to as a digital energy-integrating signal.

The inventors have realized that a signal formed from or represented by several TTOT signals is significantly more linear with input photon rate and allows the overall x-ray imaging system to maintain dose efficiency also at higher rates.

A benefit of particular non-limiting examples of the proposed method and structural configuration of obtaining a digital energy-integrating signal over the prior art of obtaining an energy integrating signal is that it does not require a dedicated analog circuit for integrating/accumulation of the signal. Instead, the inventors have realized that is feasible to utilize the digital comparator output which is already present as a part of the capability of a multi-bin photon-counting detector.

Another benefit of the proposed technology is that a signal formed from or represented by several TTOT signals includes spectral (photon energy) information which can be used for spectral imaging also for imaging cases which suffer from a high degree of pulse pileup. Such imaging tasks may possibly be performed in combination with a photon counting signal.

In other words, the proposed technology relates to Total Time-Over-Threshold (TTOT) processing for a photon-counting x-ray detector.

Other advantages will be appreciated when reading the detailed description.

BRIEF DESCRIPTION OF DRAWINGS

The embodiments, together with further objects and advantages thereof, may best be understood by making reference to the following description taken together with the accompanying drawings, in which:

FIGS. 11A-B are schematic diagrams illustrating examples of TTOT signals originating from two photons.

DETAILED DESCRIPTION

For a better understanding, it may be useful to continue with an introductory description of non-limiting examples of an overall x-ray imaging system.

Figure 2:
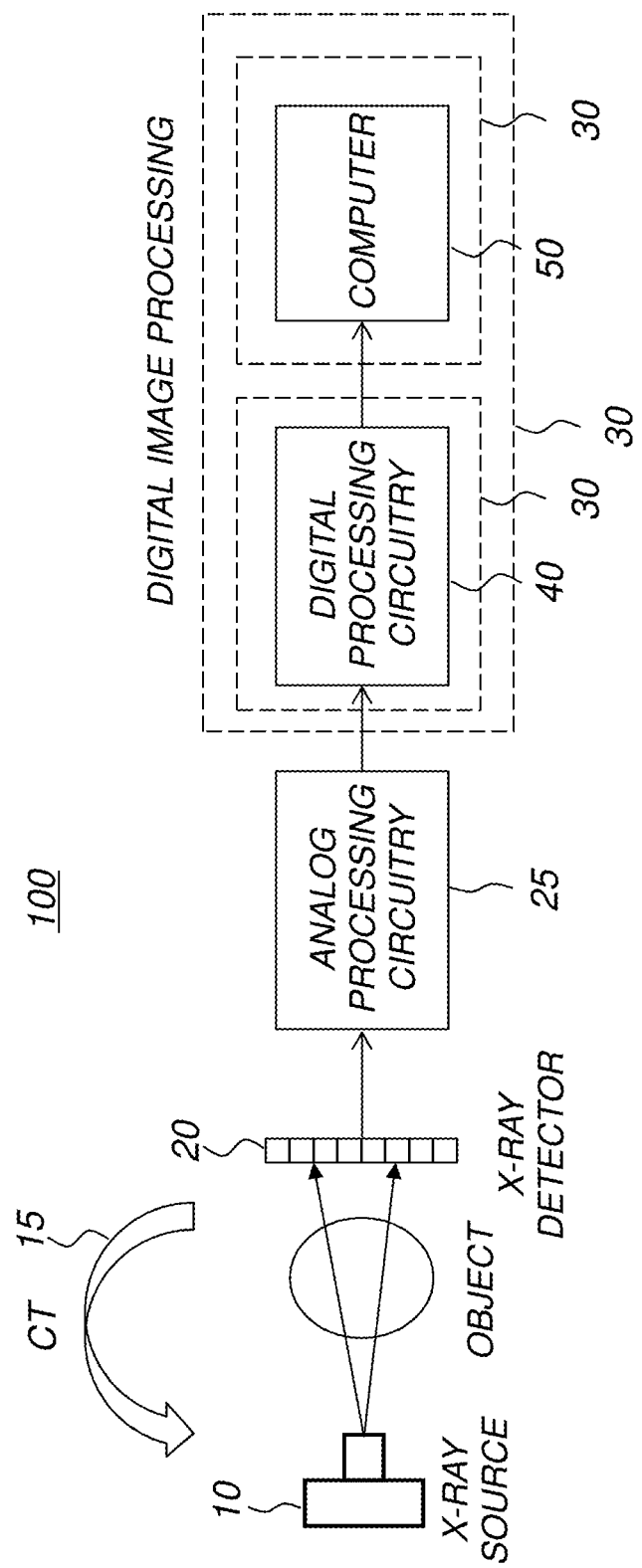
FIG. 2 is a schematic diagram illustrating another example of an x-ray imaging system.

FIG. 2 is a schematic diagram illustrating an example of an x-ray imaging system 100 comprising an x-ray source 10, which emits x-rays, an x-ray detector system 20 with an x-ray detector, which detects the x-rays after they have passed through the object, analog processing circuitry 25, which processes the raw electrical signal from the x-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. According to the invention, all or part of the analog processing circuitry 25 may be implemented in the x-ray detector system 20.

The overall x-ray detector may be regarded as the x-ray detector system 20, or the x-ray detector system 20 combined with the associated analog processing circuitry 25.

The digital part including the digital processing circuitry 40 and/or the computer 50 may be regarded as the image processing system 30, which performs image reconstruction based on the image data from the x-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used x-ray imaging system is an x-ray computed tomography, CT, system, which may include an x-ray tube that produces a fan- or cone beam of x-rays and an opposing array of x-ray detectors measuring the fraction of x-rays that are transmitted through a patient or object. The x-ray tube and detector array are mounted in a gantry that rotates around the imaged object.

Figure 3:
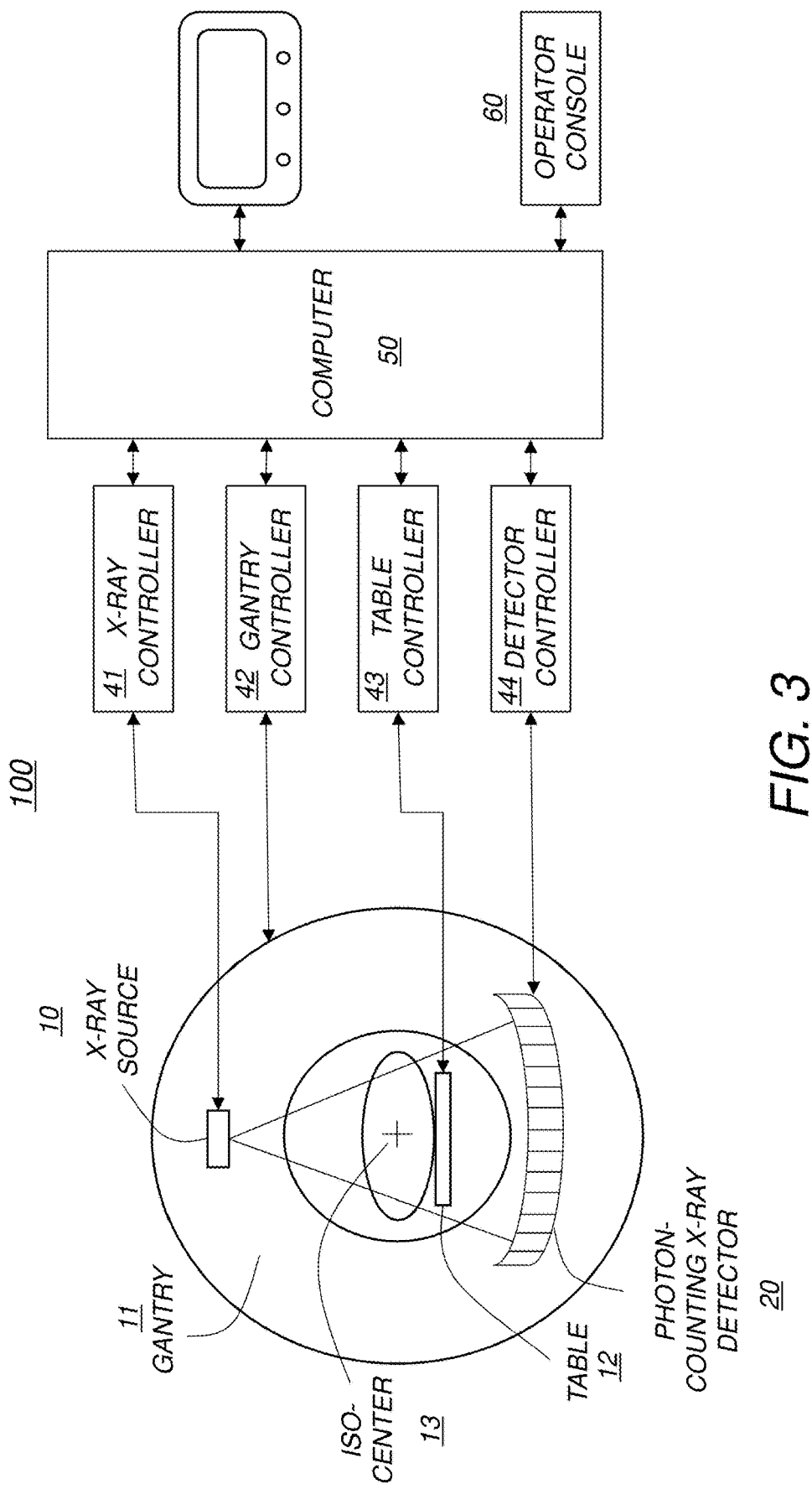
FIG. 3 is a schematic block diagram of a CT system as an illustrative example of an x-ray imaging system.

FIG. 3 is a schematic block diagram of a CT system as an illustrative example of an x-ray imaging system. The CT system comprises a computer 50 receiving commands and scanning parameters from an operator via an operator console 60 that may have a display and some form of operator interface, e.g., keyboard and mouse. The operator supplied commands and parameters are then used by the computer 50 to provide control signals to an x-ray controller 41, a gantry controller 42 and a table controller 43. To be specific, the x-ray controller 41 provides power and timing signals to the x-ray source 10 to control emission of x-rays onto the object or patient lying on the table 12. The gantry controller 42 controls the rotational speed and position of the gantry 11 comprising the x-ray source 10 and the x-ray detector 20. By way of example, the x-ray detector may be a photon-counting x-ray detector. The table controller 43 controls and determines the position of the patient table 12 and the scanning coverage of the patient. There is also a detector controller 44, which is configured for controlling and/or receiving data from the detector 20.

Figure 1:
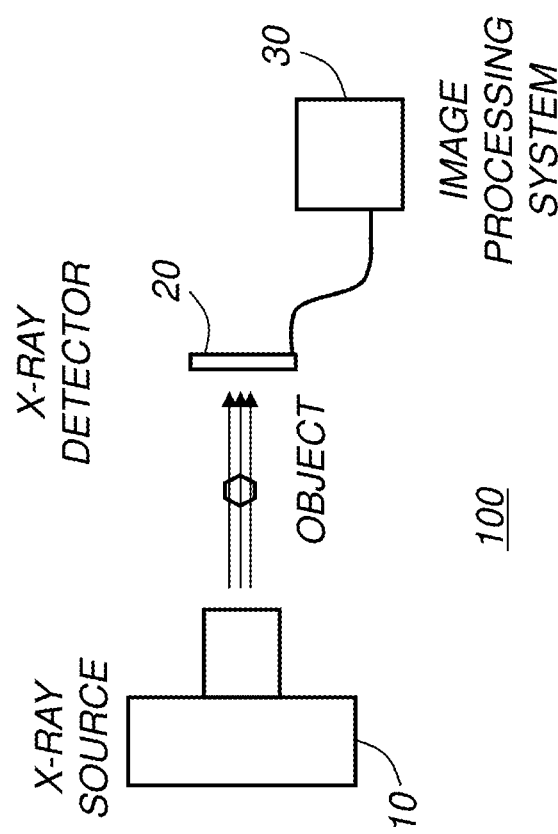
FIG. 1 is a schematic diagram illustrating an example of an overall x-ray imaging system.

In an embodiment, the computer 50 also performs post-processing and image reconstruction of the image data output from the x-ray detector. The computer thereby corresponds to the image processing system 30 as shown in FIGS. 1 and 2. The associated display allows the operator to observe the reconstructed images and other data from the computer.

The x-ray source 10 arranged in the gantry 11 emits x-rays. An x-ray detector 20, e.g. in the form of a photon-counting detector, detects the x-rays after they have passed through the patient. The x-ray detector 20 may for example be formed by plurality of pixels, also referred to as sensors or detector elements, and associated processing circuitry, such as ASICs, arranged in detector modules. A portion of the analog processing part may be implemented in the pixels, whereas any remaining processing part is implemented in, for instance, the ASICs. In an embodiment, the processing circuitry (ASICs) digitizes the analog signals from the pixels. The processing circuitry (ASICs) may also comprise a digital processing part, which may carry out further processing operations on the measured data, such as applying corrections, storing it temporarily, and/or filtering. During a scan to acquire x-ray projection data, the gantry and the components mounted thereon rotate about an iso-center.

Modern x-ray detectors normally need to convert the incident x-rays into electrons, this typically takes place through the photoelectric effect or through Compton interaction and the resulting electrons usually create secondary visible light until the energy is lost and this light is in turn detected by a photo-sensitive material. There are also detectors based on semiconductors for which the x-ray interaction results in the release of electron-hole pairs that are collected through an applied electric field.

There are detectors operating in an energy integrating mode in the sense that they provide an integrated signal from a multitude of x-rays. The output signal is proportional to the total energy deposited by the detected x-rays.

X-ray detectors with photon counting and energy resolving capabilities are becoming common for medical x-ray applications. The photon counting detectors have an advantage since in principal the energy for each x-ray photon can be measured which yields additional information about the composition of the object. This information can be used to increase the image quality and/or to decrease the radiation dose.

Generally, a photon-counting x-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter, DAC. The DAC converts a digital setting sent by a controller to an analog voltage with respect to which the heights of the photon pulses can be compared.

A photon-counting detector counts the number of photons that have interacted in the detector during a measurement time. A new photon is generally identified by that the height of the electric pulse exceeds the comparator voltage of at least one comparator. When a photon is identified, the event is stored by incrementing a digital counter associated with the channel.

When using several different threshold values, a so-called energy-discriminating photon-counting detector is obtained, in which the detected photons can be sorted into energy bins corresponding to the various threshold values. Sometimes, this type of photon-counting detector is also referred to as a multi-bin detector. In general, the energy information allows for new kinds of images to be created, where new information is available and image artifacts inherent to conventional technology can be removed. In other words, for an energy-discriminating photon-counting detector, the pulse heights are compared to a number of programmable thresholds (T1-TN) in the comparators and are classified according to pulse-height, which in turn is proportional to energy. In other words, a photon-counting detector comprising more than one comparator is here referred to as a multi-bin photon-counting detector. In the case of a multi-bin photon-counting detector, the photon counts are stored in a set of counters, typically one for each energy threshold. For example, counters can be assigned to correspond to the highest energy threshold that the photon pulse has exceeded. In another example, counters keep track of the number times that the photon pulse cross each energy threshold.

As an example, edge-on is a special, non-limiting design for a photon-counting detector, where the x-ray sensors such as x-ray detector elements or pixels are oriented edge-on to incoming x-rays.

For example, such photon-counting detectors may have pixels in at least two directions, wherein one of the directions of the edge-on photon-counting detector has a component in the direction of the x-rays. Such an edge-on photon-counting detector is sometimes referred to as a depth-segmented photon-counting detector, having two or more depth segments of pixels in the direction of the incoming x-rays.

Alternatively, the pixels may be arranged as an array (non-depth-segmented) in a direction substantially orthogonal to the direction of the incident x-rays, and each of the pixels may be oriented edge-on to the incident x-rays. In other words, the photon-counting detector may be non-depth-segmented, while still arranged edge-on to the incoming x-rays.

In order to increase the absorption efficiency, the edge-on photon-counting detector can accordingly be arranged edge-on, in which case the absorption depth can be chosen to any length, and the edge-on photon-counting detector can still be fully depleted without going to very high voltages.

A conventional mechanism to detect x-ray photons through a direct semiconductor detector basically works as follows. The energy of the x-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
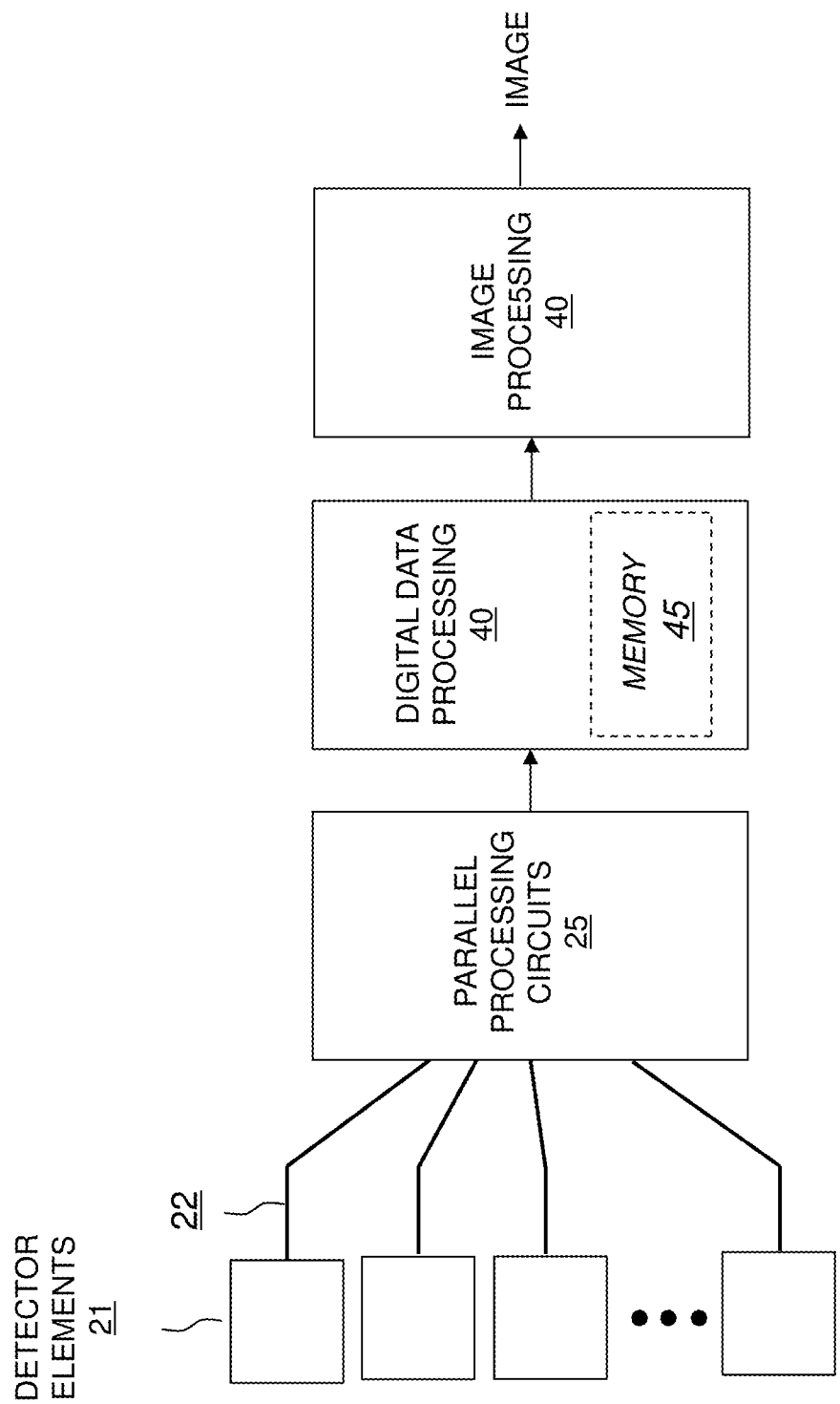
FIG. 4 is a schematic diagram illustrating another example of relevant parts of an x-ray imaging system.

As illustrated in FIG. 4, signal(s) is/are routed 22 from detector elements 21 of the x-ray detector to inputs of parallel processing circuits (e.g. ASICs) 25. It should be understood that the term Application Specific Integrated Circuit (ASIC) is to be interpreted broadly as any general circuit used and configured for a specific application. The ASIC processes the electric charge generated from each x-ray and converts it to digital data, which can be used to obtain measurement data such as a photon count and/or estimated energy. The ASICs are configured for connection to digital data processing circuitry so the digital data may be sent to further digital data processing 40 and/or one or more memories 45 and finally the data will be the input for image processing 50 to generate a reconstructed image.

As the number of electrons and holes from one x-ray event is proportional to the energy of the x-ray photon, the total charge in one induced current pulse is proportional to this energy. After a filtering step in the ASIC, the pulse amplitude is proportional to the total charge in the current pulse, and therefore proportional to the x-ray energy. The pulse amplitude can then be measured by comparing its value with one or several thresholds (THR) in one or more comparators (COMP), and counters are introduced by which the number of cases when a pulse is larger than the threshold value may be recorded. In this way it is possible to count and/or record the number of x-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing whether the comparator has been triggered (photon pulse was higher than the threshold) or not.

In a photon-counting detector, there is typically a Photon Counting Logic which determines if a new photon has been registered and, registers the photons in counter(s). In the case of a multi-bin photon-counting detector, there are typically several counters, for example one for each comparator, and the photon counts are registered in the counters in accordance with an estimate of the photon energy. The logic can be implemented in several different ways. Two of the most common categories of Photon Counting Logics are the so-called non-paralyzable counting modes, and the paralyzable counting modes [29]. Other photon-counting logics include, for example, local maxima detection, which counts, and possibly also registers the pulse height of, detected local maxima in the voltage pulse [28].

The following is an example of a non-paralyzable counting mode: 1) a new photon is detected if a threshold is triggered; 2) if a new photon is registered, a dead time is initiated during which the maximum triggered threshold is registered; 3) after the dead time has ended, a count is registered in the counter corresponding to the maximum triggered threshold; 4) the channel is open to new photons after the dead time has ended. For the non-paralyzable counting mode the registered number of counts reach a maximum value of: $N_{max}$=measurement time/dead time.

As an example of a paralyzable counting mode, take the example of the non-paralyzable counting mode and add that the duration of the dead time is extended as long as the photon pulse triggers any of the thresholds. The consequence of this change is that the number of registered counts drop to zero for very high photon count rates.

The situation when the number of incoming photons cannot be resolved by the photon-counting channel is called pulse pileup, referring to the situation that the photon pulses grow and merge together and cannot be distinguished from each other. Pulse pile-up can be a severe problem limiting the performance of photon-counting detectors [1].

There are many benefits of photon-counting detectors including, but not limited to: high spatial resolution; low electronic noise; energy resolution; and material separation capability (spectral imaging ability). However, energy-integrating detectors have the advantage of high count-rate tolerance. The count-rate tolerance comes from the fact/recognition that, since the total energy of the photons is measured, adding one additional photon will always increase the output signal (within reasonable limits), regardless of the number of photons that are currently being registered by the detector. This crucial advantage is one of the main reasons that energy-integrating detectors are the standard for medical CT today.

Several attempts have been made to combine the benefits of photon-counting and energy-integrating detectors.

An ASIC (the CIX chip) has been developed which is capable of simultaneous photon-counting (single threshold) and energy-integrating functions. The incoming signal is replicated and sent to both an energy-integrating channel and a photon-counting channel [2], [3], [4]. The ASIC has also been evaluated for its dual-energy imaging capability which it owes to the difference in energy response of the photon-counting and the energy-integrating signal [5]. It has also been suggested that an energy-integrating channel is used as back-up for the case that the photon-counting channel is saturated during a measurement time [6]. Further, there has been development towards ASICs with both photon-counting and energy-integrating acquisition available, however not simultaneously. This allows the detectors to fulfil the requirements of a large variety of x-ray experiments [7], [8].

Several patents [25] [26] [27] relate to having two parallel channels per detector element: one counting and one energy-integrating (measure of total charge collected), and a processing unit in which the signals are used in combination to determine the absorbed amount of x-rays.

Several other techniques for obtaining measurements from both an energy-integrating and a photon-counting detector have been developed. For example, a dual-detector system having both an energy-integrating and a photon-counting detector has been developed and evaluated for imaging [9]. Patent US 2012/0085915 A1 [24] describes a detector with detector elements comprising a photon-counting part and an energy-integrating part.

Another concept that has been proposed involves having a detector with energy-integrating and photon-counting pixel elements interleaved, i.e. each pixel is either photon-counting or energy-integrating [10]. Yet another approach is to combine thresholding of the signal, to obtain energy resolution, and charge integration, to simplify the electronic circuits [11].

Measuring the time-over-threshold (TOT), i.e. the duration that a pulse is above a comparator threshold, has been used extensively as a means of measuring the energy of individual particles [12], [13], [14], [15], [16], [17]. To improve the resolution of the energy and the arrival-time of detected particles, it has been proposed to analyze the TOT signal for several thresholds at different voltages simultaneously. The so-called multi-time-over-threshold, MTOT, technique has been used for various applications such as: photomultiplier signal processing, neutrino telescopes, positron emission tomography (PET) and cosmic ray detection [18], [19], [20], [21].

In reference [22] it is shown that the total time-over-threshold (TTOT) readout can be used to enhance the dynamic range of the photon-counting detector; the TTOT signal saturates slower than the photon-counting signal. The detector described in the reference can operate the time-over-threshold mode, but not simultaneously with the counting mode. The TOT mode has a specific circuit implementation and a command can be sent to the ASIC to switch into this mode. There is a patent describing a method of using a total-time-over-threshold (TTOT) in combination with a paralyzable photon-counting detector to improve the high count-rate performance [23]. The described method obtains a total-time-over-threshold value by means of a separate high-flux electronic circuit. The electronic circuit can be configured to integrate an analog voltage signal which is switched on when the voltage pulse exceeds a threshold and vice versa. The electronic TTOT measurement circuit can also be implemented by associating a counter with the comparator and incrementing the counter each clock-cycle for which the comparator is triggered.

For a better understanding of the proposed measurement method, it may be useful to begin with a brief system overview and/or analysis of the technical problem. To this end, reference is made to FIG. 5, which provides a schematic illustration of a photon-counting circuit and/or device according to prior art.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g. ASICs. It should be understood that the term Application Specific Integrated Circuit, ASIC, is to be interpreted broadly as any general circuit used and configured for a specific application. The ASIC processes the electric charge generated from each x-ray and converts it to digital data, which can be used to obtain measurement data such as a photon count and/or estimated energy. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the input voltage pulse to a reference voltage (corresponding to an energy threshold). The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters, DAC, 301 can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

Figure 6:
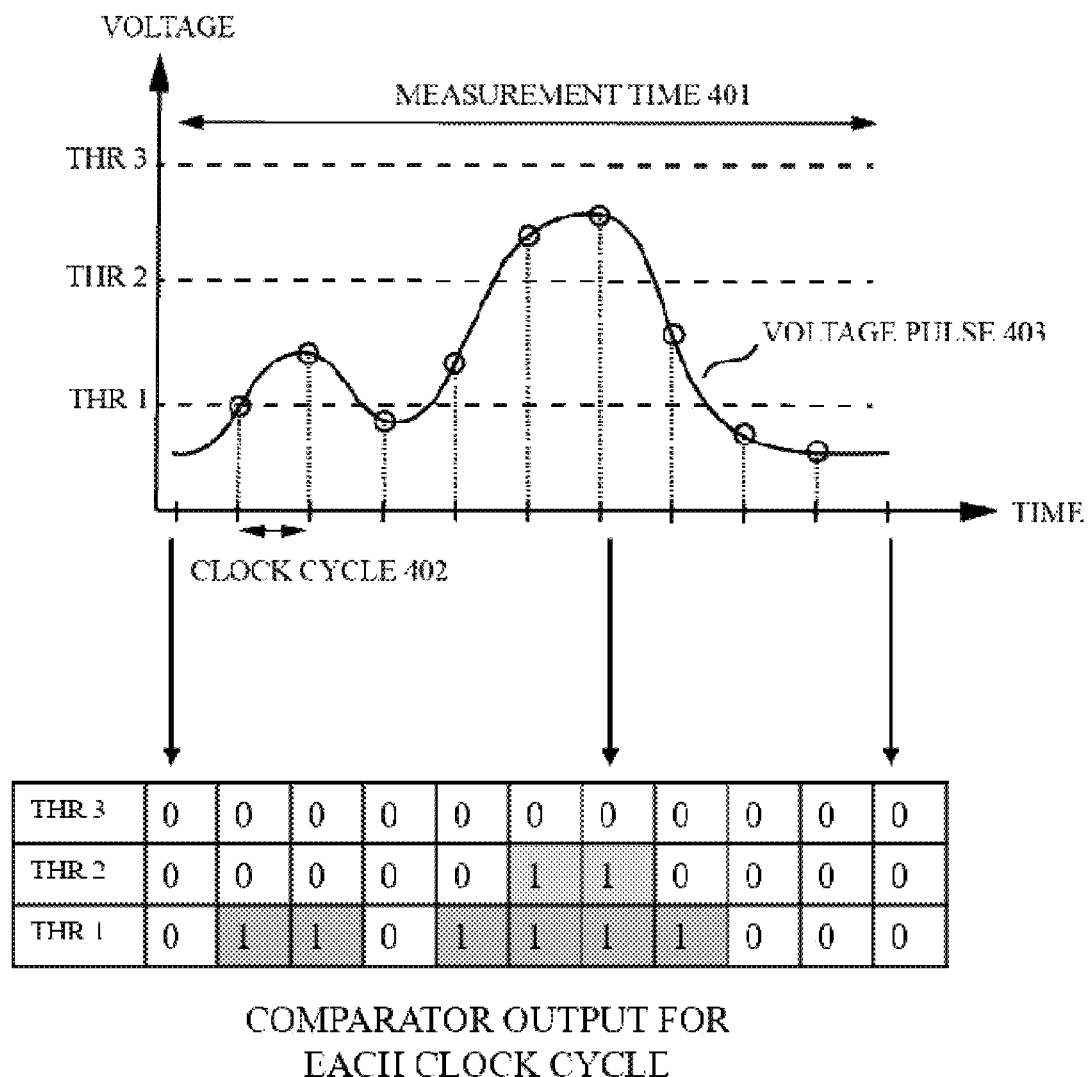
FIG. 6 is a schematic diagram illustrating an example of pulse voltage over time, and corresponding comparator output per clock cycle.

For reference, FIG. 6 illustrates an example of a signal analyzed by the ASIC. The ASIC generally comprises an ASIC clock that determines the rate at which the comparator output is sampled. The sampling interval is here referred to as a Clock Cycle 402, and the length of one clock cycle is typically on the order of 10 ns. During each clock cycle, the output of each comparator is sampled by the ASIC. For example, if the channel comprises 5 comparators, the ASIC receives one binary number for each comparator at each clock cycle indicating whether the corresponding comparator is triggered or not. In other words, at each clock cycle, the ASIC receives information about which thresholds that the voltage pulse 403 currently exceeds. In the example in FIG. 6, the ASIC receives information in accordance with the table: a set of ones and/or zeros for each threshold (THR1, THR2, THR3) indicating whether the voltage pulse 403 exceeds the threshold.

Conventionally, it is often not feasible to read out the output from the comparators for each clock cycle due to limitations in the data transfer chain. Instead, the ASIC aggregates a representation of the comparator output during a Measurement Time 401. The measurement time is typically on the order of 100 µs. As an example, with a 10 ns clock cycle, and 100 µs measurement time, there are 10,000 clock cycles per measurement time. In the example in FIG. 6, the measurement time is 11 clock cycles long. The aggregated representation of the comparator output can, for example, be photon counts registered in accordance to a photon counting logic. Another example is to register each time that the voltage pulse crosses a threshold level in the upward direction, i.e. the comparator output switches from zero (0) to one (1). In the example in FIG. 6, the voltage pulse crosses THR1 in the upward direction two times, and THR2 one time.

Figures 10A, 10B:
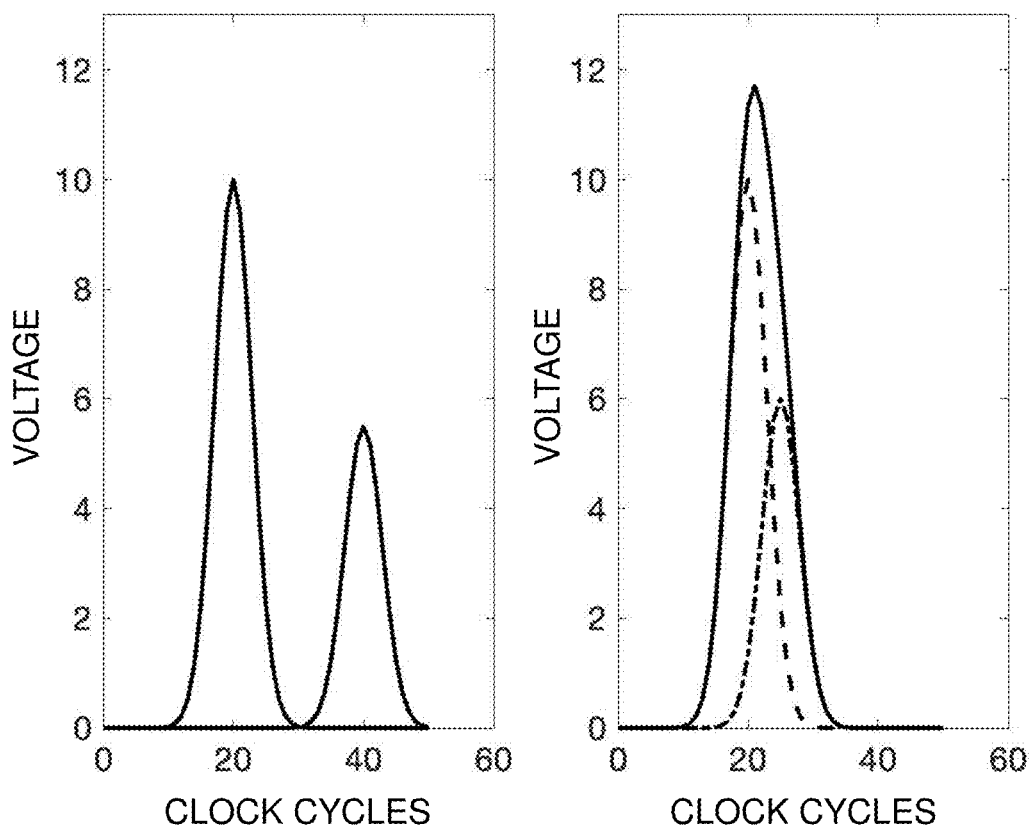
FIGS. 10A-B are schematic diagrams illustrating examples of the voltage pulses of two photons which arrive in close vicinity in time.

FIGS. 10A-B are schematic diagrams illustrating examples of the voltage pulses of two photons which arrive in close vicinity in time. In FIG. 10A, the two pulses are clearly separated, whereas in FIG. 10B, the two pulses add up forming a single, larger, voltage pulse. This phenomena is referred to as pulse pileup, and for a photon-counting detector, this degrades the signal in two ways: firstly, the event is registered as one count, instead of two, resulting in a loss of statistics, which negatively affects the system dose efficiency, and secondly the event is registered at a wrong energy, distorting the spectral fidelity of the measurement and impairing the system's spectral imaging ability.

According to a first aspect, there is provided a circuit configured for operation with a multi-bin photon-counting x-ray detector having multiple energy thresholds. The circuit is configured to obtain or generate several Total Time-Over-Threshold (TTOT) signals corresponding to several different energy thresholds, and provide energy integrating information based on said several TTOT signals.

Figure 7:
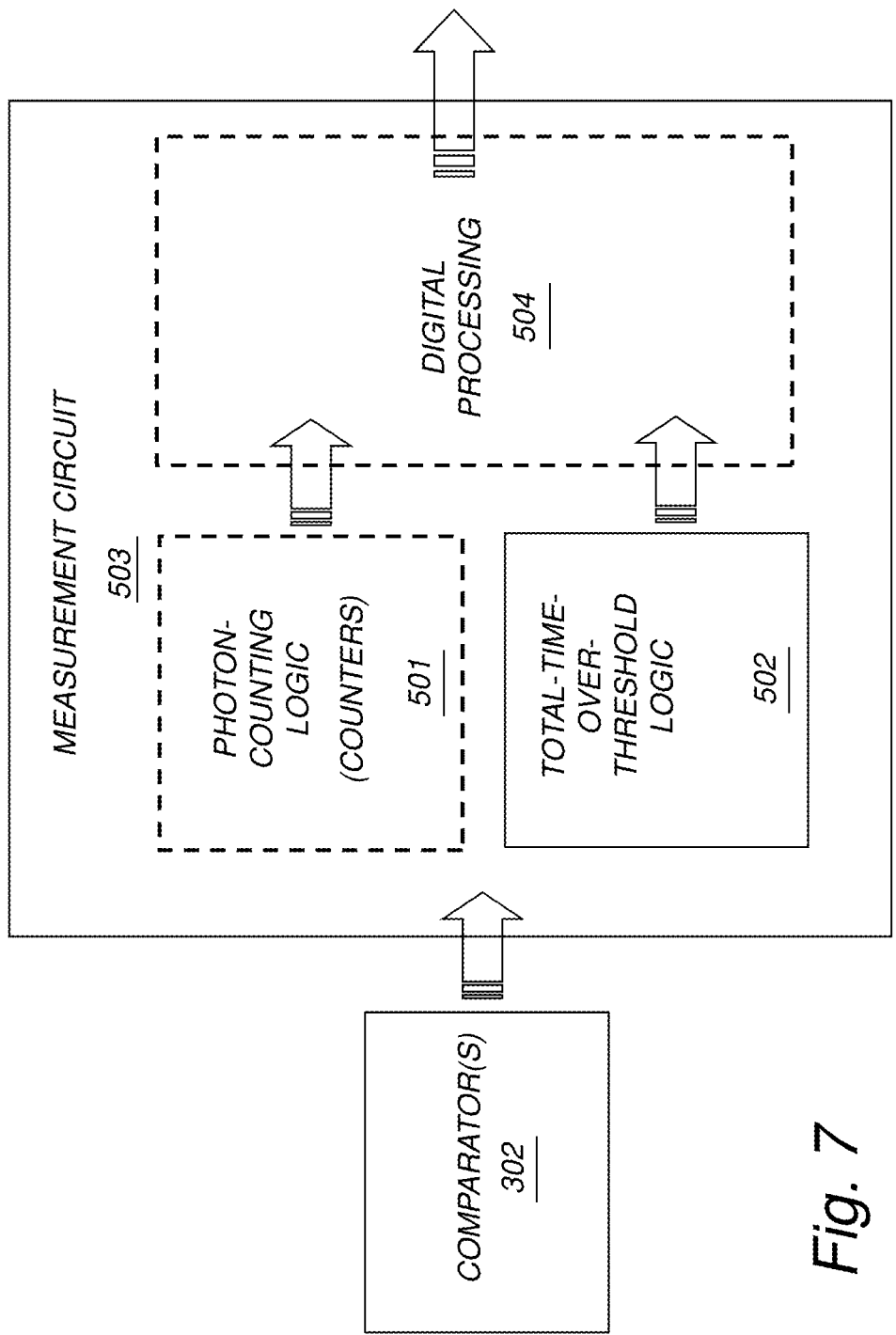
FIG. 7 is a schematic diagram illustrating an example of measurement circuitry, including at least a total-time-over-threshold (TTOT) logic, applied directly on the comparator output.
Figure 8A:
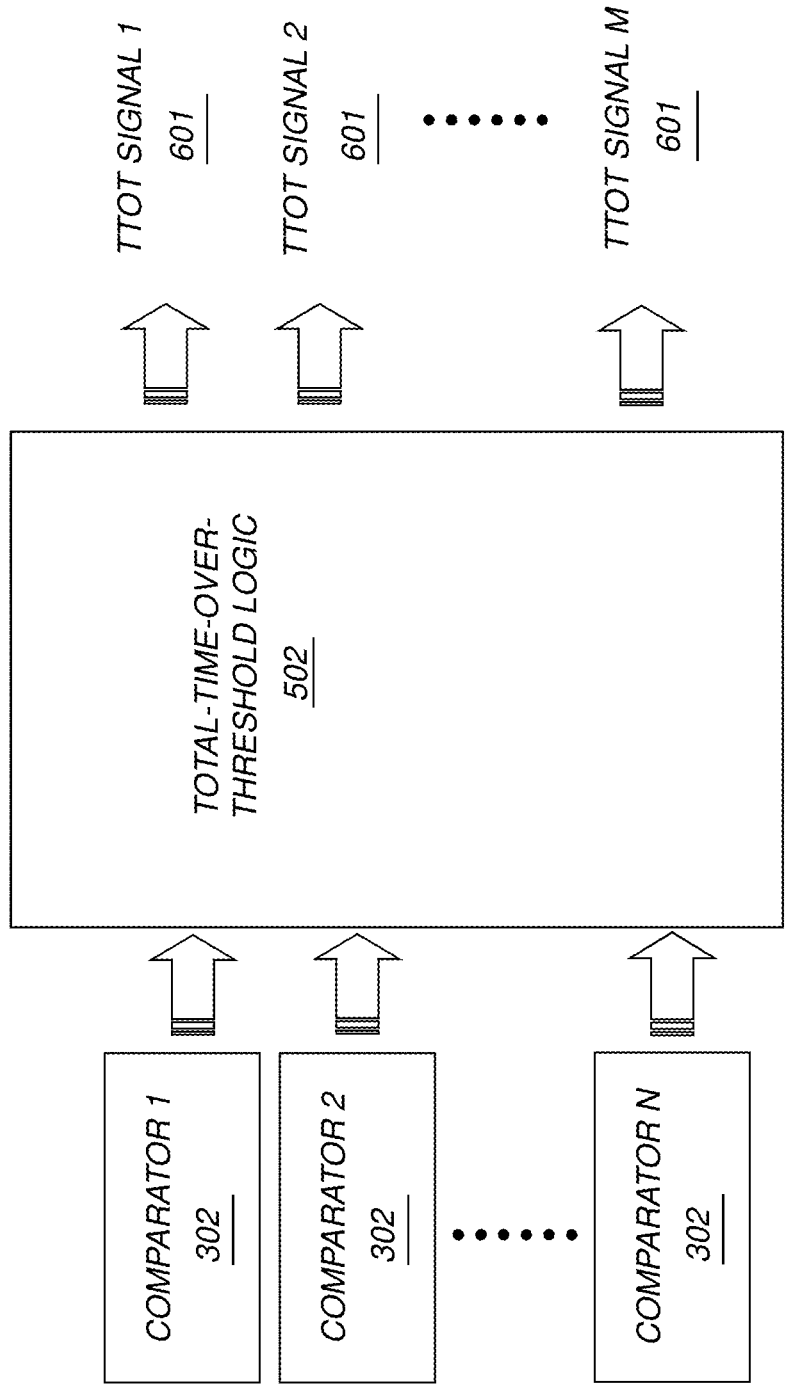
FIG. 8A is a schematic diagram illustrating an example of total-time-over-threshold (TTOT) circuitry for generating several Total Time-Over-Threshold (TTOT) signals corresponding to several different energy thresholds.
Figure 8B:
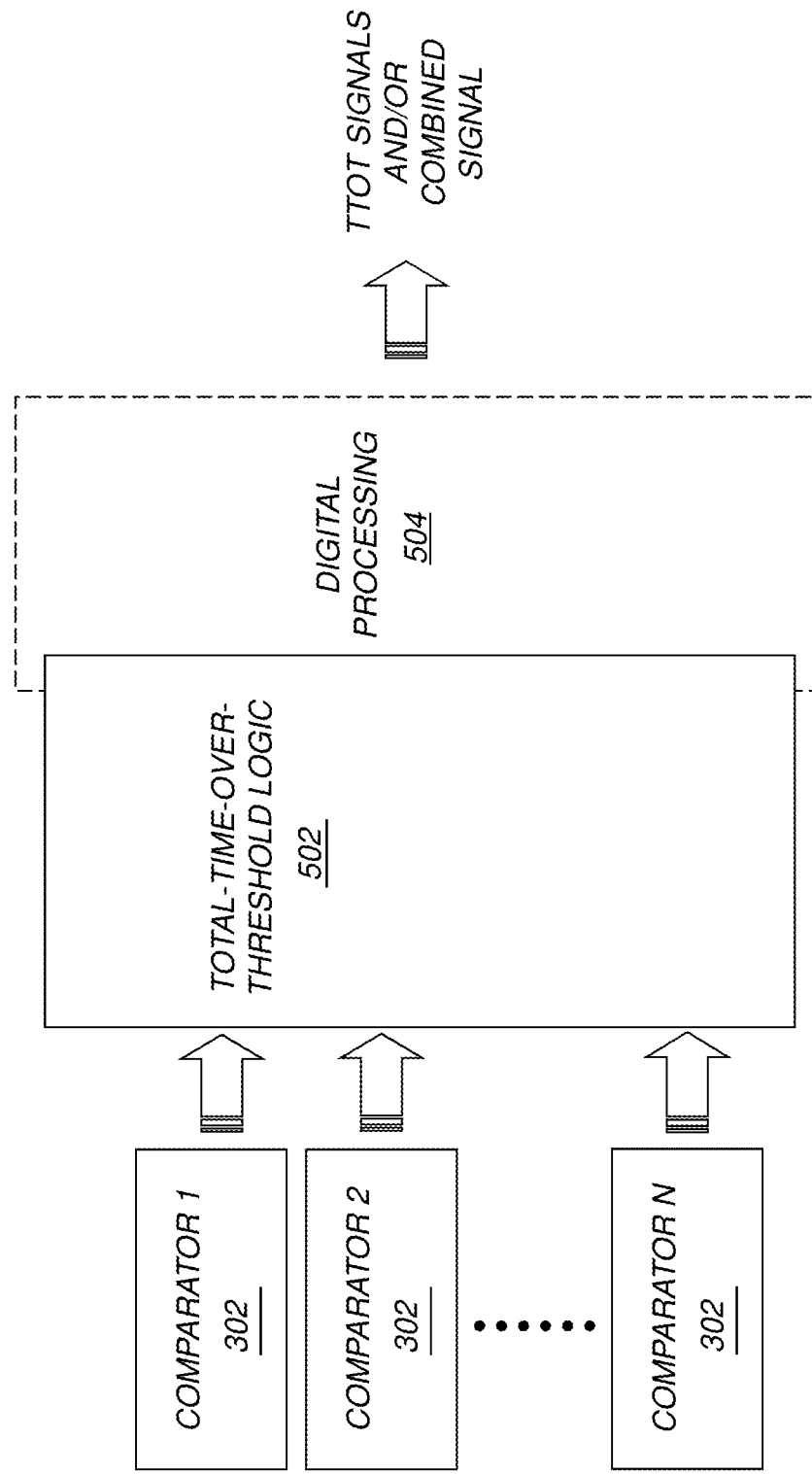
FIG. 8B is a schematic diagram illustrating another example of a system/circuitry for obtaining and/or generating more than one TTOT signal.
Figure 9:
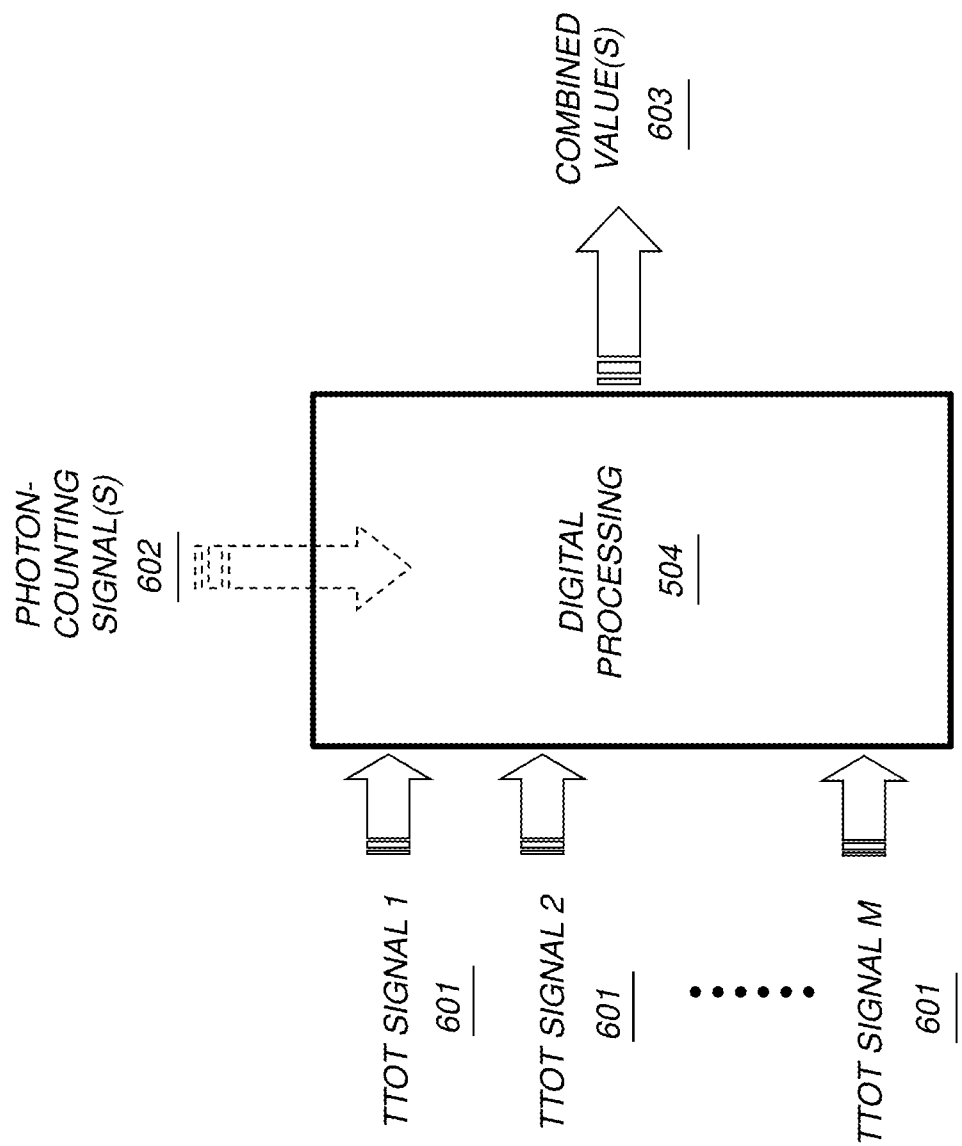
FIG. 9 is a schematic diagram illustrating an example of digital processing circuitry for generating at least one combined value from more than one TTOT signal, and optionally one or more photon counting signals.

This corresponds to general circuitry which may be implemented in various forms, e.g. as one or more individual circuits and/or may include a set of individual circuits and/or various sub-circuits, non-limiting examples of which are schematically illustrated in FIG. 7 and FIGS. 8A-B and/or FIG. 9.

By way of example, the circuit may be configured to provide energy integrating information formed from or represented by said several TTOT signals.

In a particular example, the circuit is configured to form a signal that approximates or represents an energy integrating signal based on said TTOT signals for said several energy thresholds set at different energies.

For example, the circuit may be configured to form or generate a digital energy-integrating signal by (weighted) summation or, linear or non-linear combination of said several TTOT signals.

Alternatively, or as a complement, the circuit may be configured to output the energy integrating information via said several TTOT signals, e.g. more or less directly for image reconstruction.

Interestingly, the aggregation and/or combination of said several TTOT signals may include spectral energy information.

In a particular example, the circuit is configured to be applied directly on comparator output of said multi-bin photon-counting x-ray detector, e.g. as schematically illustrated in FIG. 7 and FIGS. 8A-B.

By way of example, the circuit may be configured to generate or obtain said TTOT signals corresponding to several different energy thresholds based on comparator output from corresponding comparators of the multi-bin photon-counting x-ray detector as input (e.g. see FIG. 7 and FIGS. 8A-B).

Figure 5:
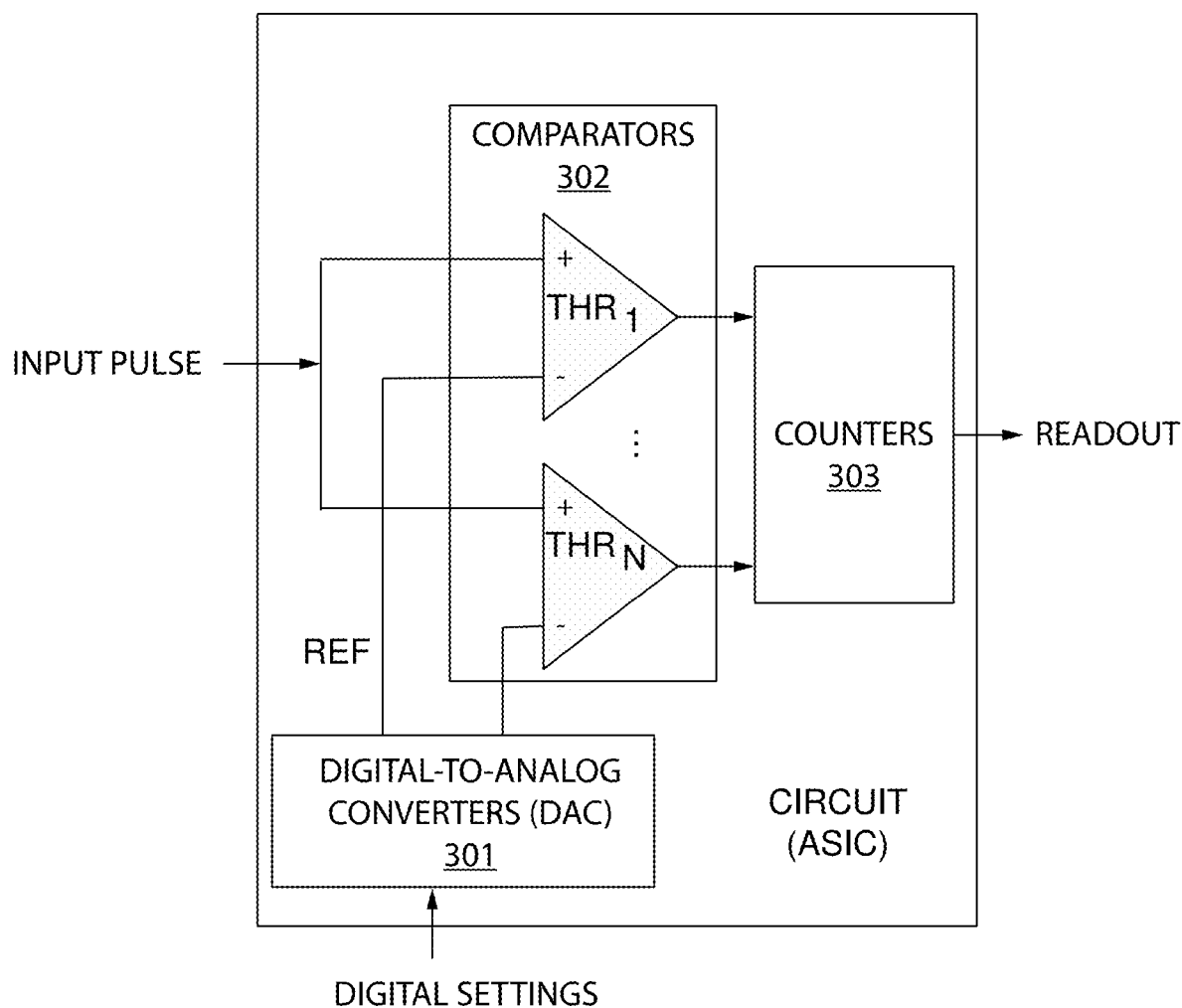
FIG. 5 is a schematic illustration of a photon-counting circuit and/or device according to prior art.

Referring back to the particular example of FIG. 5, each comparator may be configured to operate based on a respective energy threshold.

The multi-bin photon-counting x-ray detector may have a set of comparators 302, each comparator being configured to compare the magnitude of an input voltage pulse from one or more detector elements to a reference voltage corresponding to a respective energy threshold to produce a comparator output.

For example, the circuit may be configured to generate or obtain each of the TTOT signals based on input including the total number of clock cycles during which an input voltage pulse exceeds a reference voltage during a predetermined measurement time or a subset thereof in a respective comparator.

In a particular example, the circuit may be configured to generate or obtain each of the TTOT signals from comparator output by summing the number of clock cycles that a respective comparator is triggered during a predetermined measurement time or a subset thereof.

Optionally, the circuit may be configured to sum comparator outputs for more than one, i.e. several, comparators during the measurement time or a subset thereof, or the circuit may be configured to compute a mean value of comparator outputs during the measurement time or a subset thereof, or the circuit may be configured to compute the sum of the clock cycles during which each comparator is the highest triggered comparator.

It is also possible for the circuit to be configured to generate or obtain said several TTOT signals for a sub-set of the available energy thresholds and/or for a sub-set of detector elements of the x-ray detector.

By way of example, the circuit includes a Total Time-Over-Threshold (TTOT) logic circuit 502 and/or a digital processing circuit 504.

According to a second aspect, there is provided a Total Time-Over-Threshold (TTOT) logic circuit configured for operation with a multi-bin photon-counting x-ray detector having multiple energy thresholds, wherein said TTOT logic circuit is configured to generate several Total Time-Over-Threshold (TTOT) signals corresponding to several different energy thresholds, and provide energy integrating information based on said several TTOT signals.

As an example, the TTOT logic circuit may be configured to provide energy integrating information formed from or represented by said several TTOT signals.

By way of preferable example, the TTOT logic circuit may be configured to be applied directly on comparator output of the multi-bin photon-counting x-ray detector.

For example, the TTOT logic circuit may be configured to sample the comparator output of the photon-counting x-ray detector at a sampling interval.

In a particular example, the TTOT logic circuit is configured to generate said TTOT signals corresponding to several different energy thresholds based on comparator output from corresponding comparators of the multi-bin photon-counting x-ray detector as input.

According to a third aspect, there is provided a digital processing circuit configured for operation with a multi-bin photon-counting x-ray detector having multiple energy thresholds, wherein the digital processing circuit is configured to obtain more than one Total Time-Over-Threshold (TTOT) signal corresponding to more than one energy threshold, and provide energy integrating information based on said more than one TTOT signal.

For example, the digital processing circuit may be configured to receive said more than one TTOT signal and form a combined value representing at least said energy integrating information based on said more than one TTOT signal.

In a particular example, the digital processing circuit is configured to combine TTOT signals from low and high energy thresholds to form said combined value.

By way of example, the digital processing circuit may be configured to receive said more than one TTOT signal and at least one photon-counting signal, and form a combined value representing energy integrating information and photon-counting information by signal combination.

As an example, the digital processing circuit may be configured to form said combined value by signal combination dependent on the rate of incoming x-ray photons.

Optionally, the digital processing circuit may be configured to form said combined value by giving added weight to said at least one photon-counting signal in said signal combination at photon rates lower than a predetermined threshold rate and giving added weight to said more than TTOT signal in said signal combination at photon rates higher than said threshold rate.

According to a fourth aspect, there is provided a measurement circuit for a photon-counting x-ray detector comprising a TTOT logic circuit of the second aspect and/or a digital processing circuit of the third aspect.

Optionally, the measurement circuit further comprises a photon-counting logic circuit, e.g. as schematically illustrated in FIG. 7.

In a particular example, the measurement circuit is configured to sample the comparator output of the photon-counting x-ray detector at a sampling interval.

According to a fifth aspect, there is provided an x-ray imaging system comprising a circuit of any of the first aspect, second aspect, third aspect and/or fourth aspect.

By way of example, the x-ray imaging system may be configured to perform material specific imaging of an object to be imaged based on the TTOT signals from several energy thresholds as spectral information.

For example, the x-ray imaging system may be configured to perform material specific imaging of an object to be imaged based on the TTOT signals in combination with a photon-counting signal and/or a digital energy-integrating signal formed from the TTOT signals.

According to a sixth aspect, there is provided a system configured for operation with a multi-bin photon-counting x-ray detector having multiple energy thresholds, wherein the system is configured for generating more than one Total Time-Over-Threshold (TTOT) signal based on the output from more than one comparator of the multi-bin photon-counting detector.

As mentioned, it is thus possible to obtain a signal that represents or approximates an energy integrating signal based on total-time-over-threshold (TTOT) signals for several energy thresholds set at different energies in a multi-bin photon-counting x-ray detector. Such a signal may be referred to as a digital energy-integrating signal.

The inventors have realized that a signal formed from or represented by several TTOT signals is significantly more linear with input photon rate and allows the overall x-ray imaging system to maintain dose efficiency also at higher rates.

A benefit of particular non-limiting examples of the proposed method and structural configuration of obtaining a digital energy-integrating signal over the prior art of obtaining an energy integrating signal is that it does not require a dedicated analog circuit for integrating/accumulation of the signal. Instead, the inventors have realized that is feasible to utilize the digital comparator output which is already present as a part of the capability of a multi-bin photon-counting detector.

In the following, non-limiting examples will be described in more detail.

In a particular embodiment, the invention is related to obtaining a signal that represents or approximates an energy integrating signal based on total-time-over-threshold (TTOT) signals 601 for several energy thresholds set at different energies in a multi-bin photon-counting detector. The obtained signal will herein be referred to as a digital energy-integrating signal.

The digital energy-integrating signal can for example be formed by a summation, linear, or non-linear, combination of the TTOT signals corresponding to several energy thresholds. The energy integration information can also be passed indirectly via the several TTOT signals to an image reconstruction process.

A benefit of the proposed method of obtaining a digital energy-integrating signal over the prior art of obtaining an energy integrating signal is that it does not require a dedicated analog circuit for integrating/accumulation of the signal. Instead, the method takes advantage of the digital comparator output which is already present as a part of the capability of a multi-bin photon-counting detector.

A signal formed from or represented by several TTOT signals is significantly more linear with input photon rate and maintains dose efficiency also at higher rates.

A benefit of the proposed method is that the several TTOT signals contains spectral (photon energy) information which can be used for spectral imaging also for imaging cases which suffer from a high degree of pulse pileup.

Also, the invention relates to using the TTOT signal from several energy thresholds as spectral information for performing material separation (material specific imaging) of the imaged object. Possibly in combination with a photon-counting signal, and/or a digital energy-integrating signal.

In an example embodiment, the photon-counting logic is non-paralyzable.

Figure 12:
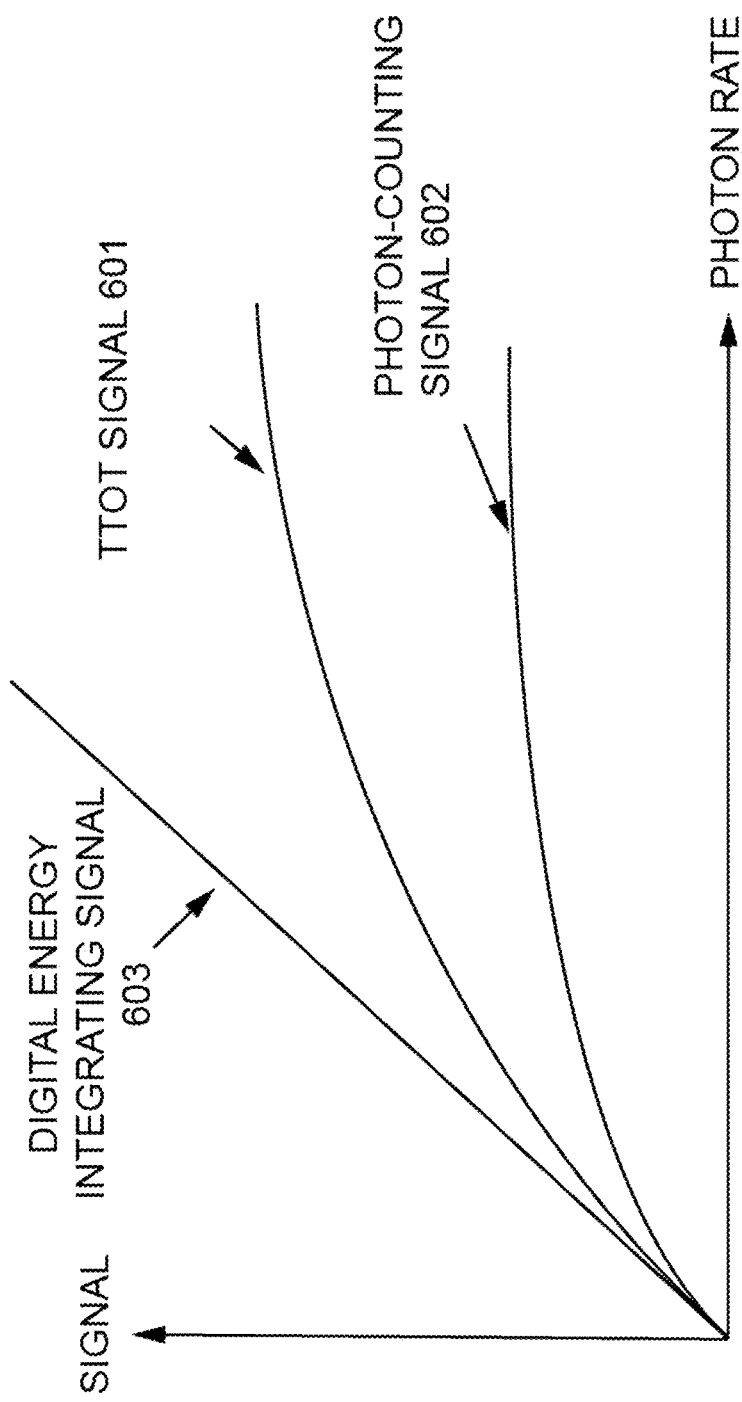
FIG. 12 is a schematic diagram illustrating an example of how a photon-counting signal saturates (loses signal) at lower photon rates than a TTOT signal, which in turn saturates a lower photon rates than a digital energy-integrating signal.

A specific purpose of the invention may be to improve the performance of the multi-bin photon-counting detector at high photon rates. This is illustrated in FIG. 12, where it is shown that the photon-counting signal 602 (here with non-paralyzable photon-counting logic) saturates (loses signal) at lower photon rates than the TTOT signal 601, which in turn saturates at lower photon rates than the digital energy-integrating signal 603. The main reason for this behavior is that the TTOT signal does not operate with a dead-time during which no signal can be registered. Therefore, adding additional photon pulses generally increases the measured TTOT signal also in presence of pulse pileup. The digital energy integrating signal increases in proportion to the number of photons up to very high photon rates.

In an embodiment of the invention, (each of) the total-time-over-threshold (TTOT) signals 601 are based on the total number of clock cycles 402 during which an input voltage pulse exceeds a reference voltage during a measurement time 401. A basic idea is to extract TTOT signals from comparator output by for example summing the number of clock cycles that a comparator is triggered during a measurement time. With reference to FIG. 6, the sum of the triggered clock cycles during the measurement time is six (6) for THR1 and two (2) for THR2.

A benefit of the proposed method to extract TTOT signals over the prior art is that it does not require a dedicated analog electronic circuit to estimate the TTOT signal. Instead, a total-time-over-threshold counting logic is applied directly on the comparator output. This is illustrated in FIG. 7, where the output from the comparators 302 is sent to a measurement circuit comprising a total-time-over-threshold logic 502 and, in an example embodiment, an (optional) photon counting logic 501. The output from the TTOT logic and the photon-counting logic is in one example embodiment optionally passed through a step of digital processing 504 prior to read-out from the measurement circuit 503.

According to another aspect, an example embodiment of the current invention also relates to a total-time-over-threshold counting logic 502, and corresponding device and/or system. In an example embodiment the total-time-over-threshold (TTOT) logic can be implemented as a sum of the comparator outputs for the more than one, i.e. several, comparators during the measurement time. In an alternative embodiment, the TTOT logic computes a mean value of comparator outputs during the measurement time. In an additional embodiment, the TTOT logic computes the sum of the clock cycles during which each comparator is the highest triggered comparator. With reference to FIG. 6, the later embodiment would return 4 for THR1 and 2 for THR2.

According to yet another aspect, an example embodiment of the current invention also relates to a measurement circuit 503 comprising both a photon-counting logic 501 and total-time-over-threshold logic 502, as illustrated in FIG. 7. The measurement circuit 503 can be implemented to output both photon-counting output, and TTOT output, or any combination thereof via a step of digital processing 504. It should be understood that the invention is not limited by the particular implementation of the photon-counting logic. For example, the photon-counting logic can be either paralyzable, or non-paralyzable.

Referring to FIG. 8A, the current invention also relates to a method/system for obtaining and/or generating more than one TTOT signal 601 based on the output for more than one comparator 302 in a multi-bin photon counting detector.

In an example embodiment, TTOT signals 601 are obtained for a sub-set of the available energy thresholds. In an additional embodiment, TTOT signals 601 are obtained for a sub-set of the detector elements. In an additional embodiment, the TTOT signals are measured during a sub-set of the measurement time.

FIG. 8B is a schematic diagram illustrating another example of a system/circuitry for obtaining and/or generating more than one TTOT signal. In this particular example, the system/circuitry may optionally involve a digital processing circuit 504 in addition to the TTOT logic circuit 502 to generate the TTOT signals and/or a combined value or signal.

FIG. 9 is a schematic diagram illustrating an example of digital processing circuitry for generating at least one combined value from more than one TTOT signal, and optionally one or more photon counting signals.

The current invention also relates to a method/system/circuitry for forming at least one combined value 603 from more than one TTOT signal 601. The combined value being, for example, a weighted sum of the TTOT values. The combined value can also include a photon-counting signal 602 in an effort to obtain the benefits of both signals. The combined value can be an approximation of an energy-integrating signal, via, for example, a weighted sum of TTOT values where the weights represent the distance between two adjacent comparator voltages. The selected method of signal combination can be, for example, dependent on the rate of incoming x-ray photons. For example, at low photon rates (i.e. below a given threshold rate), the photon-counting signal out-performs the TTOT signals, and it is therefore beneficial to give added weight to the photon-counting signal. At high photon rates or flux (i.e. above a given threshold rate), on the other hand, the TTOT signal outperforms the photon-counting signal, and added weight can therefore be given to the TTOT signal.

FIGS. 11A-B are schematic diagrams illustrating examples of TTOT signals originating from two photons.

An example of the TTOT signals 601 from a measurement comprising two photon pulses separated in time is shown in FIG. 11A. In this example, the TTOT signal for each threshold is formed by a sum of the number of clock cycles during which the threshold was triggered. In FIG. 11A, the two photon pulses are clearly separated, and in FIG. 11B, the two photon pulses are added together forming a single, larger, voltage pulse. For each case, the TTOT signal 601 is indicated in the table to the right of the figure. We can see that the TTOT signal for low-energy thresholds (THR1 and THR2) decrease as a consequence of the pulse pileup. For high-energy thresholds (THR3, THR4 and THR5), on the other hand, the TTOT signal increases.

According to still another aspect, an example embodiment of the invention relates to a method of forming a combined value from TTOT signals corresponding to several thresholds at different energy. In a particular example, the method of forming a combined value which represents or approximates the integral of the voltage pulse during the measurement time. In an example embodiment, the combined value is formed by computing a weighted sum of several TTOT signals. The weights can be selected such that the combined value that represents or approximates the integral of the voltage pulse. In the example in FIG. 11, consider the weights: [3, 2, 2, 2, 2] for TTOT signals corresponding to thresholds 1, 2, 3, 4, 5 respectively. The weights correspond to the distance between the energy thresholds. The weighted sum would in this case be equal to the integral of the bar diagram in FIG. 11, which approximates the true voltage pulse quite closely. The weighted sum would in this case approximate the integral of the voltage pulse. In the particular example in FIG. 11, the weighted sum amounts to 102 for case A and 103 for case B, indicating, as desired, that the combined signal is relatively insensitive to pulse pileup. An alternative weighting scheme is to, for each threshold, compute the total number of clock cycles $N_i$ during which threshold i is the highest triggered threshold. If the average height of the pulse when threshold i is the highest triggered threshold is $H_i$, then the integral of the voltage pulse can be approximated by sum($N_i \times H_i$) for all thresholds (i). The values of $H_i$ can be estimated from knowledge of the location of the energy thresholds, and the values Ni can be computed either directly from the comparator values in the TTOT logic, or by computing Ni=$TTOT_i-TTOT_{i+1}$, where $TTOT_i$ is the total number of clock cycles during which threshold i was triggered.

A benefit of measuring the TTOT signal for several thresholds at different energy levels is that the TTOT signals saturate (lower signal than ideal) at different rates; the higher the threshold voltage is, the slower the signal saturates since fewer photons have high energy. In the case of pulse pile-up, the TTOT signal for a low energy threshold 601 starts to saturate. The TTOT signal for a high-energy threshold 601 can increase as a consequence of pile-up. The behavior of the TTOT signal as a function of increasing photon rate is demonstrated in FIG. 13. This is due to the fact that the combined pulse of two or more photons have a higher amplitude than each individual pulse, thus triggering higher thresholds more often, which can be concluded from FIG. 11. In a sense, the decreased TTOT signal for a low threshold due to pulse pile-up is compensated by an increased TTOT signal for higher thresholds. In other words, there are two competing features of the signal as the photon rate is increased: the decreasing average pulse length, and the increasing average pulse height. At low energies, the decreasing average pulse length dominates, and at high energies the increasing average pulse height dominates. The total energy, which is proportional to the integral of the voltage pulse, is on the other hand linear with increasing photon rate.

To understand why a TTOT signal for a comparator at a low energy saturates with increasing photon rate, consider a case in which two photon pulses arrive at the channel in close vicinity in time, closer than the width of the individual pulses. The two pulses form a combined pulse whose length is larger than each individual pulse, however, shorter than the sum of the length of the two pulses. The TTOT signal is therefore not linear with increasing photon rate but increases slower than linear. At extremely high count-rates, the TTOT signal approaches a maximum value equal to the measurement time.

Figure 13:
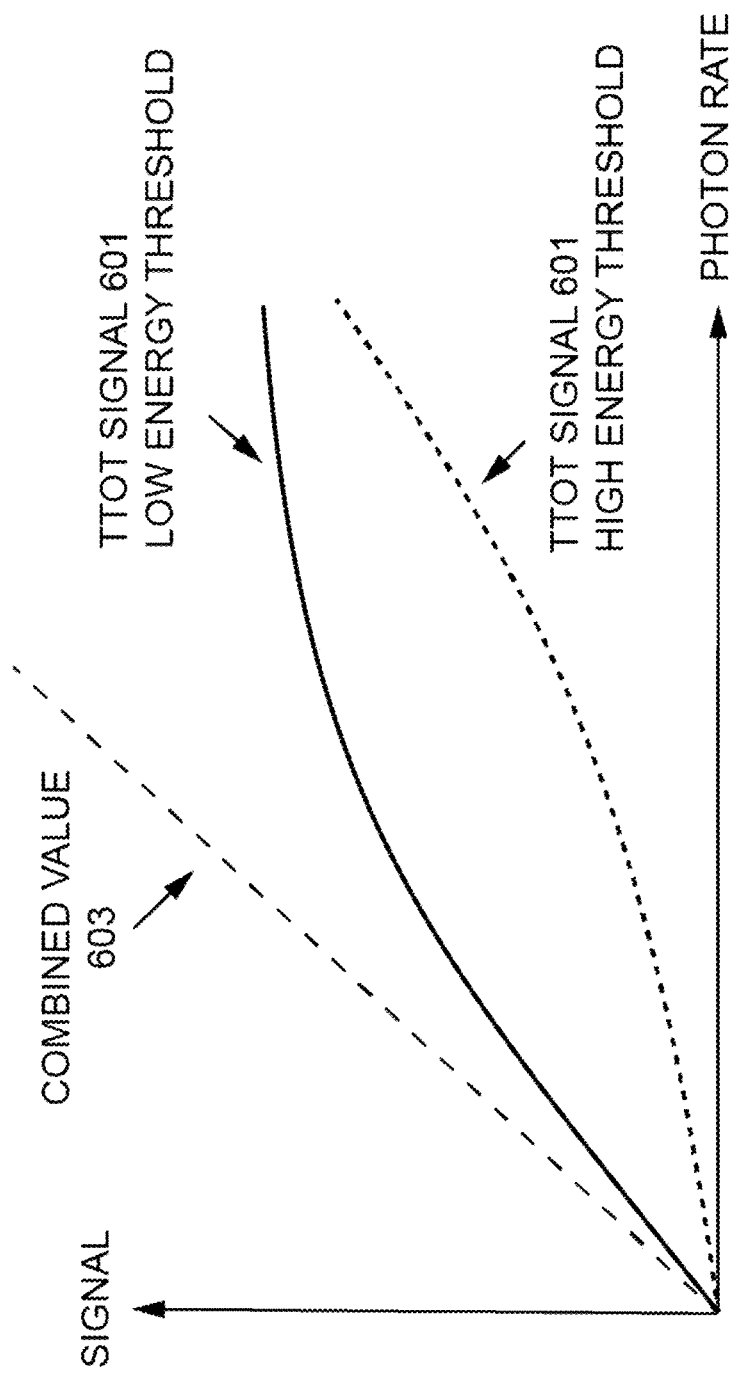
FIG. 13 is a schematic diagram illustrating an example of the behavior of a TTOT signal as a function of increasing photon rate.

If TTOT signals 601 from low and high energy thresholds are combined, it is possible to form a combined value 603 that is linear with the rate of incoming photons, as illustrated in FIG. 13. The linearity comes from the configuration and/or design that the high and low TTOT signals 601 are combined to form a signal that is proportional to the total deposited energy during the measurement time. The linear signal resembles the signal from an energy integrating detector, with the difference that the integration is performed on the digitized signal rather than the analog signal.

In order to have good photon detection efficiency, i.e. a large fraction of the photons is registered, it is desirable to have at least one threshold set at a low energy such that also low-energy photons are registered. If only one threshold is used, the threshold will generally be set at a relatively low energy. As a consequence, the TTOT signal of the single comparator will saturate at relatively low photon count-rates.

The output from each detector element (photon-counting and TTOT signals) can be read out from the x-ray Imaging System and analyzed after read-out, or be analyzed in a processing unit located, for example, in the ASIC, or in a field programable gate array (FPGA).

The method can be used to obtain simultaneous spectral photon-counting, and energy integrating data, without the need for two separate channels per pixel.

Compared to a TTOT approach using a single threshold, the combined value 603 based on several TTOT signals 601 can be configured to have higher count-rate resistance. Also, having several TTOT signals can improve the spectral imaging ability at higher count rates.

According to another aspect, there is provided a multi-bin photon counting detector for which a least a sub-set of the detector elements can obtain a photon-counting signal and a TTOT signal.

According to another aspect, there is provided an x-ray imaging system comprising an x-ray source and an x-ray detector comprising an array of photon counting detectors configured to obtain TTOT signals and photon-counting signals for at least a sub-set of the detector elements.

According to a complementary aspect, there is provided an x-ray detector and an x-ray imaging system, comprising a photon-counting silicon edge-on detector which is configured to obtain TTOT signals and photon-counting signals for at least a sub-set of the detector elements.

Figure 14:
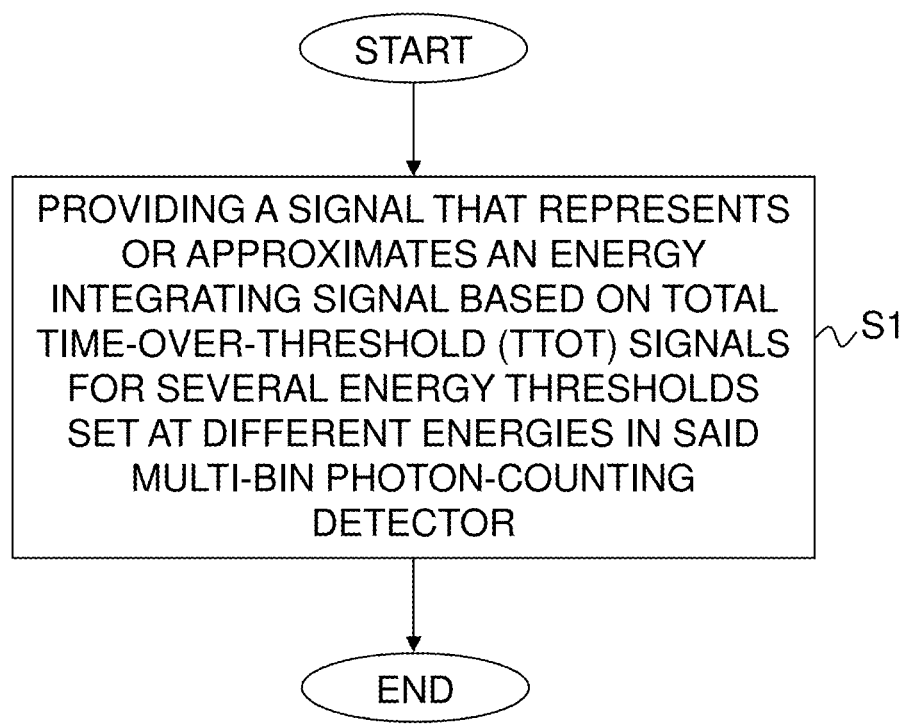
FIG. 14 is a schematic diagram illustrating an example of a method obtaining energy integrating information from a multi-bin photon-counting x-ray detector.

FIG. 14 is a schematic diagram illustrating an example of a basic method obtaining energy integrating information from a multi-bin photon-counting x-ray detector.

Basically, the method comprises the step S1 of providing or generating a signal that represents or approximates an energy integrating signal based on Total Time-Over-Threshold (TTOT) signals for several energy thresholds set at different energies in said multi-bin photon-counting detector.

It will be appreciated that the mechanisms and arrangements described herein can be implemented, combined and re-arranged in a variety of ways.

For example, embodiments may be implemented in hardware, or at least partly in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

According to a complementary aspect, there is provided a corresponding computer program and computer-program product.

In particular, there is provided a computer program comprising instructions, which when executed by a processor, cause the processor to perform the method as described herein.

For example, there may also be provided a computer-program product comprising a non-transitory computer-readable medium having stored thereon such a computer program.

Figure 15:
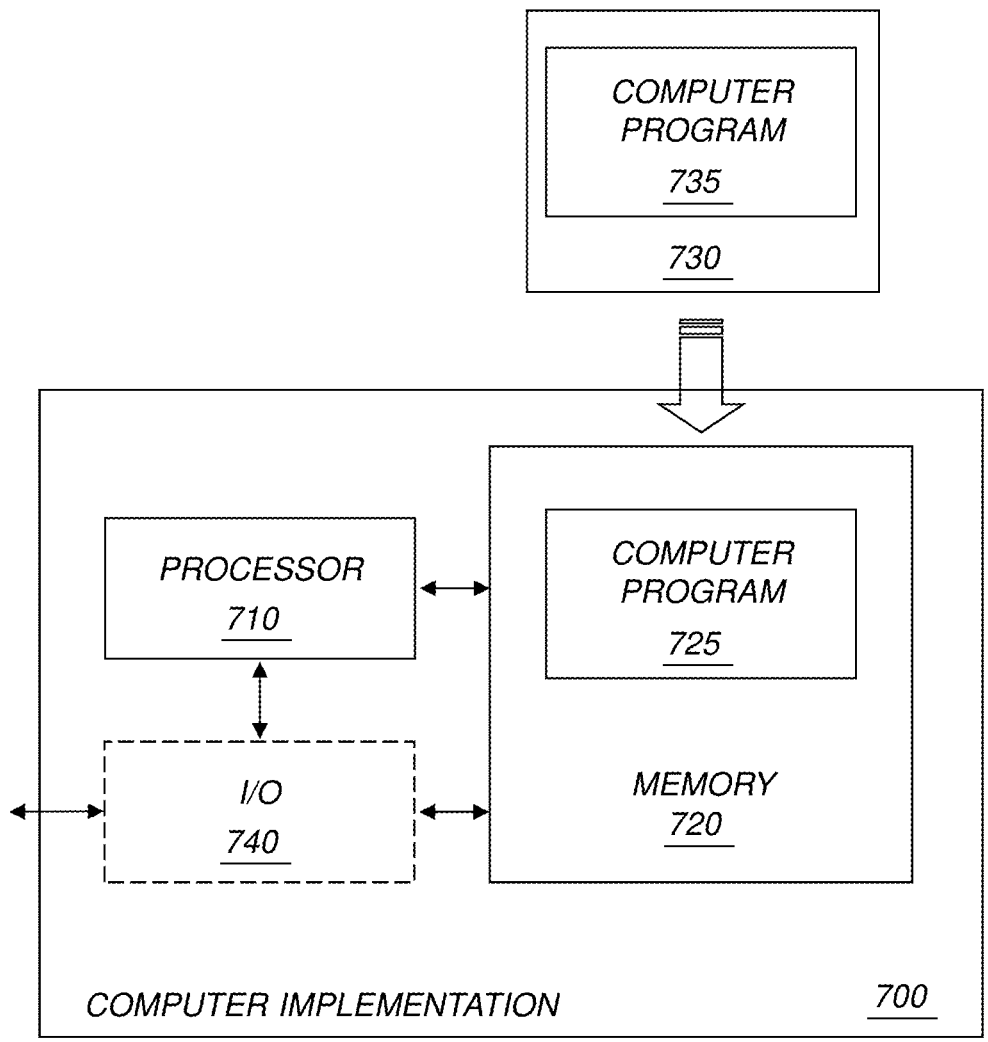
FIG. 15 is a schematic diagram illustrating an example of a computer implementation according to an embodiment.

FIG. 15 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

In a particular example, the memory comprises such a set of instructions executable by the processor, whereby the processor is operative to determine an estimate or measure of charge diffusion and estimate the initial point of interaction along the thickness of the detector sub-module based on the determined estimate of charge diffusion.

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possible to realize the modules predominantly by hardware modules, or alternatively by hardware. The extent of software versus hardware is purely implementation selection.

When the proposed technology is used for performing material specific imaging based on the spectral information contained in the several TTOT signals, basis material decomposition techniques may be utilized.

Basis material decomposition utilizes the fact that all substances built up from elements with low atomic number, such as human tissue, have linear attenuation coefficients μ(E) whose energy dependence can be expressed, to a good approximation, as a linear combination of two (or more) basis functions:

$$\mu(E) = a_1 f_1(E) + a_2 f_2(E).$$

where $f_i$ are the basis functions and $a_i$ are the corresponding basis coefficients. If there is one or more element in the imaged volume with high atomic number, high enough for a k-absorption edge to be present in the energy range used for the imaging, one basis function must be added for each such element. In the field of medical imaging, such k-edge elements can typically be iodine or gadolinium, substances that are used as contrast agents.

Basis material decomposition, in general, has been described in Alvarez and Macovski, "Energy-selective reconstructions in X-ray computerised tomography", Phys. Med. Biol. 21, 733. In basis material decomposition, the line integral $A_i$ of each of the basis coefficients $a_i$ is inferred from the measured data in each projection ray l from the source to a detector element. The line integral $A_i$ can be expressed as:

$$A_i = \int_l a_i dl \text{ for } i = 1, \ldots, N,$$

where N is the number of basis functions. In one implementation, basis material decomposition is accomplished by first expressing the expected registered number of counts in each energy bin as a function of $A_i$. Typically, such a function may take the form:

$$\lambda_i = \int_{E=0}^{\infty} S_i(E) \exp\left(-\sum_{j=1}^{N} A_j f_j(E)\right) dE$$

Here, $\lambda_i$ is the expected number of counts in energy bin i, E is the energy, $S_i$ is a response function which depends on the spectrum shape incident on the imaged object, the quantum efficiency of the detector and the sensitivity of energy bin i to x-rays with energy E. Even though the term "energy bin" is most commonly used for photon-counting detectors, this formula can also describe other energy resolving x-ray systems such as multi-layer detectors or kVp switching sources.

Then, the maximum likelihood method may be used to estimate $A_i$ under the assumption that the number of counts in each bin is a Poisson distributed random variable. This is accomplished by minimizing the negative log-likelihood function, see Roessl and Proksa, K-edge imaging in x-ray computed tomography using multi-bin photon counting detectors, Phys. Med. Biol. 52 (2007), 4679-4696:

$$\hat{A}_1, \ldots, \hat{A}_N = \underset{A_1, \ldots, A_N}{\operatorname{argmin}} \sum_{i=1}^{M_b} \lambda_i(A_1, \ldots, A_N) - m_i \ln \lambda_i(A_1, \ldots, A_N)$$

where $m_i$ is the number of measured counts in energy bin i and $M_b$ is the number of energy bins.

From the line integrals A, a tomographic reconstruction to obtain the basis coefficients $a_i$ may be performed. This procedural step may be regarded as a separate tomographic reconstruction, or may alternatively be seen as part of the overall basis decomposition.

When the resulting estimated basis coefficient line integral $\hat{A}_i$ for each projection line is arranged into an image matrix, the result is a material specific projection image, also called a basis image, for each basis i. This basis image can either be viewed directly (e.g. in projection x-ray imaging) or taken as input to a reconstruction algorithm to form maps of basis coefficients a, inside the object (e.g. in CT). Anyway, the result of a basis decomposition can be regarded as one or more basis image representations, such as the basis coefficient line integrals or the basis coefficients themselves.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

[1] S. S. Hsieh, P. L. Rajbhandary, and N. J. Pelc, "Spectral resolution and high-flux capability tradeoffs in CdTe detectors for clinical CT," Medical physics, vol. 45, no. 4, pp. 1433-1443, 2018.

[2] E. Kraft, P. Fischer, M. Karagounis, M. Koch, H. Krueger, I. Peric, N. Wermes, C. Herrmann, A. Nascetti, M. Overdick et al., "Counting and integrating readout for direct conversion x-ray imaging: Concept, realization and first prototype measurements," IEEE Transactions on Nuclear Science, vol. 54, no. 2, pp. 383-390, 2007.

[3] H. Krüger, J. Fink, E. Kraft, N. Wermes, P. Fischer, I. Peric, C. Herrmann, M. Overdick, and W. Rütten, "Cix: a detector for spectrally enhanced x-ray imaging by simultaneous counting and integrating," in Medical Imaging 2008: Physics of Medical Imaging, vol. 6913. International Society for Optics and Photonics, 2008, p. 69130P.

[4] J. Fink, E. Kraft, H. Kruger, N. Wermes, K. J. Engel, and C. Herrmann, "Comparison of pixelated cdznte, CdTe and Si sensors with the simultaneously counting and integrating cix chip," IEEE Transactions on Nuclear Science, vol. 56, no. 6, pp. 3819-3827, 2009.

[5] E. Roessl, C. Herrmann, E. Kraft, and R. Proksa, "A comparative study of a dual-energy-like imaging technique based on counting-integrating readout," Medical physics, vol. 38, no. 12, pp. 6416-6428, 2011. [6] C. Herrmann, "x-ray detector with saturated sensor element estimated photon counting," Jun. 13, 2017, U.S. Pat. No. 9,678,220.

[7] W. S. Wong, G. Anton, R. Ballabriga, G. Blaj, M. Bohnel, M. Campbell, T. Gabor, E. Heijne, X. Llopart, T. Michel et al., "Electrical measurements of a multi-mode hybrid pixel detector asic for radiation detection," Journal of Instrumentation, vol. 7, no. 01, p. C01056, 2012.

[8] A. Bergamaschi, R. Dinapoli, B. Henrich, I. Johnson, A. Mozzanica, X. Shi, and B. Schmitt, "Beyond single photon counting x-ray detectors," Nuclear Instruments and Methods in Physics Research Section A: Accelerators, Spectrometers, Detectors and Associated Equipment, vol. 628, no. 1, pp. 238-241, 2011.

[9] S. Kappler, T. Hannemann, E. Kraft, B. Kreisler, D. Niederloehner, K. Stierstorfer, and T. Flohr, "First results from a hybrid prototype ct scanner for exploring benefits of quantum-counting in clinical ct," in Medical Imaging 2012: Physics of Medical Imaging, vol. 8313. International Society for Optics and Photonics, 2012, p. 83130X.

[10] J. Chu, W. Cong, L. Li, and G. Wang, "Combination of current integrating/photon-counting detector modules for spectral ct," Physics in Medicine & Biology, vol. 58, no. 19, p. 7009, 2013.

[11] L. Li, Z. Chen, W. Cong, and G. Wang, "Spectral ct modeling and reconstruction with hybrid detectors in dynamic-threshold-based counting and integrating modes," IEEE transactions on medical imaging, vol. 34, no. 3, pp. 716-728, 2014.

[12] T. Akesson, E. Arik, K. Assamagan, K. Baker, E. Barberio, D. Barberis, H. Bertelsen, V. Bytchkov, J. Callahan, A. Catinaccio et al., "Particle identification using the time-over-threshold method in the atlas transition radiation tracker," Nuclear Instruments and Methods in Physics Research Section A: Accelerators, Spectrometers, Detectors and Associated Equipment, vol. 474, no. 2, pp. 172-187, 2001.

[13] X. Llopart, R. Ballabriga, M. Campbell, L. Tlustos, and W. Wong, "Timepix, a 65 k programmable pixel readout chip for arrival time, energy and/or photon counting measurements," Nuclear Instruments and Methods in Physics Research Section A: Accelerators, Spectrometers, Detectors and Associated Equipment, vol. 581, no. 1-2, pp. 485-494, 2007.

[14] J. Jakubek, "Precise energy calibration of pixel detector working in time over-threshold mode," Nuclear Instruments and Methods in Physics Research Section A: Accelerators, Spectrometers, Detectors and Associated Equipment, vol. 633, pp. S262-S266, 2011.

[15] W. S. Wong, G. Anton, R. Ballabriga, M. Bohnel, M. Campbell, E. Heijne, X. Llopart, T. Michel, I. Munster, R. Plackett et al., "A pixel detector asic for dosimetry using time-over-threshold energy measurements," Radiation Measurements, vol. 46, no. 12, pp. 1619-1623, 2011. [16] K. Shimazoe, H. Takahashi, B. Shi, T. Orita, T. Furumiya, J. Ooi, and Y. Kumazawa, "Dynamic time over threshold method," IEEE Transactions on Nuclear Science, vol. 59, no. 6, pp. 3213-3217, 2012.

[17] W. Yonggang, C. Xinyi, L. Deng, Z. Wensong, and L. Chong, "A linear time-over-threshold digitizing scheme and its 64-channel daq prototype design on fpga for a continuous crystal pet detector," IEEE transactions on nuclear science, vol. 61, no. 1, pp. 99-106, 2014. [18] G. Bourlis, A. Leisos, A. Tsirigotis, S. Tzamarias, K. N. Consortium et al., "Use of multi-time over threshold electronics to digitize signals from a very large volume undersea neutrino telescope," Nuclear Instruments and Methods in Physics Research Section A: Accelerators, Spectrometers, Detectors and Associated Equipment, vol. 626, pp. S163-S165, 2011.

[19] S. Ferry, F. Guilloux, S. Anvar, F. Chateau, E. Delagnes, V. Gautard, F. Louis, E. Monmarthe, H. Le Provost, S. Russo et al., "Multi-timeover-threshold technique for photomultiplier signal processing: Description and characterization of the SCOTT asic," Nuclear Instruments and Methods in Physics Research Section A: Accelerators, Spectrometers, Detectors and Associated Equipment, vol. 695, pp. 52-60, 2012.

[20] K. B. Kim, Y. Choi, J. Jung, S. Lee, H.-j. Choe, and H. T. Leem, "Analog and digital signal processing method using multi-time-over threshold and fpga for pet," Medical physics, vol. 45, no. 9, pp. 4104-4111, 2018.

[21] K. Georgakopoulou, C. Spathis, G. Bourlis, A. Tsirigotis, A. Leisos, M. Birbas, A. Birbas, and S. E. Tzamarias, "A 100 ps multi-time over threshold data acquisition system for cosmic ray detection," Measurement Science and Technology, vol. 29, no. 11, p. 115001, 2018.

[22] A. Bergamaschi, R. Dinapoli, D. Greiffenberg, B. Henrich, I. Johnson, A. Mozzanica, V. Radicci, B. Schmitt, X. Shi, and L. Stoppani, "Time over-threshold readout to enhance the high flux capabilities of single photon-counting detectors," Journal of synchrotron radiation, vol. 18, no. 6, pp. 923-929, 2011.

[23] U.S. Pat. No. 9,535,167B2, R. Proksa and R. S. Booker, "High flux photon counting detector electronics," 2017

[24] US20120085915A1, Christian Baeumer, Guenter Zeitler, Klaus Juergen Engel, Christoph Herrmann, Roger Steadman Booker, "Processing electronics and method for determining a count result, and detector for an x-ray imaging device", 2008

[25] EP1231485A2, X ray detector with a wide dynamic range, Michael Dr. Philips C.I.P. GmbH OverdickWalter Dr. Philips C.I.P. GmbH RüttenThomas Dr. Philips C.I.P. GmbH Zaengel, 2001

[26] US20090304149A1, x-ray detector imaging with polychromatic spectra, Christoph Herrmann, Guenter Zeitler, Christian Baeumer, Klaus Jurgen Engel, 2006

[27] US20140328465A1, x-ray detector, Christoph Herrmann, 2012

[28] Scott S. Hsieh and Norbert J. Pelc, "Improving pulse detection in multibin photon-counting detectors", Journal of Medical Imaging 3.2: 023505, 2016

[29] Tenney F H, "Idealized pulse pileup effects on energy spectra", Nuclear Instruments and Methods in Physics Research 219(1), 165-172, 1984

The invention claimed is:

1. A digital processing circuit configured for operation with a multi-bin photon-counting x-ray detector having multiple energy thresholds, wherein the digital processing circuit is configured to obtain more than one Total Time-Over-Threshold (TTOT) signal corresponding to more than one energy threshold, and provide energy integrating information based on said more than one TTOT signal, wherein the digital processing circuit is configured to receive said more than one TTOT signal and form a combined value representing at least said energy integrating information based on said more than one TTOT signal.

2. The digital processing circuit of claim 1, wherein the digital processing circuit is configured to combine TTOT signals from low and high energy thresholds to form said combined value.

3. A measurement circuit for a photon-counting x-ray detector comprising the digital processing circuit of claim 1.

4. An x-ray imaging system comprising the digital processing circuit of claim 1.

5. The x-ray imaging system of claim 4, wherein the x-ray imaging system is configured to perform material specific imaging of an object to be imaged based on the TTOT signals from several energy thresholds as spectral information, and/or the x-ray imaging system is configured to perform material specific imaging of an object to be imaged based on the TTOT signals in combination with a photon counting signal and/or a digital energy integrating signal formed from the TTOT signals.

6. A digital processing circuit configured for operation with a multi-bin photon-counting x-ray detector having multiple energy thresholds, wherein the digital processing circuit is configured to obtain more than one Total Time-Over-Threshold (TTOT) signal corresponding to more than one energy threshold, and provide energy integrating information based on said more than one TTOT signal, wherein the digital processing circuit is configured to receive said more than one TTOT signal and at least one photon-counting signal, and form a combined value representing energy integrating information and photon-counting information by signal combination.

7. The digital processing circuit of claim 6, wherein the digital processing circuit is configured to form said combined value by signal combination dependent on the rate of incoming x-ray photons, and the digital processing circuit is configured to form said combined value by giving added weight to said at least one photon-counting signal in said signal combination at photon rates lower than a predetermined threshold rate and giving added weight to said more than one TTOT signal in said signal combination at photon rates higher than said threshold rate.

8. A measurement circuit for a photon-counting x-ray detector comprising the digital processing circuit of claim 6.

* * * * *